US010101352B2

(12) United States Patent
Borodkin et al.

(10) Patent No.: US 10,101,352 B2
(45) Date of Patent: Oct. 16, 2018

(54) SAMPLE SELECTOR

(71) Applicant: Brooks Automation, Inc., Chelmsford, MA (US)

(72) Inventors: Mark Borodkin, San Diego, CA (US); David Mejia, Oceanside, CA (US); Werner Willemse, Poway, CA (US); Robert K. Neeper, Ramona, CA (US)

(73) Assignee: Brooks Automation, Inc., Chelmsford, MA (US)

( * ) Notice: Subject to any disclaimer, the term of this patent is extended or adjusted under 35 U.S.C. 154(b) by 0 days.

(21) Appl. No.: 15/496,989

(22) Filed: Apr. 25, 2017

(65) Prior Publication Data

US 2017/0227561 A1 Aug. 10, 2017

Related U.S. Application Data

(62) Division of application No. 14/229,077, filed on Mar. 28, 2014, now Pat. No. 9,630,775.

(51) Int. Cl.
| | |
|---|---|
| *G01N 35/02* | (2006.01) |
| *G01N 35/00* | (2006.01) |
| *B65G 1/137* | (2006.01) |
| *G01N 35/04* | (2006.01) |

(52) U.S. Cl.
CPC ........... *G01N 35/026* (2013.01); *B65G 1/137* (2013.01); *G01N 35/0099* (2013.01); *G01N 2035/0465* (2013.01)

(58) Field of Classification Search
USPC ....................................................... 700/218
See application file for complete search history.

(56) References Cited

U.S. PATENT DOCUMENTS

| | | | |
|---|---|---|---|
| 2007/0172396 A1 | 7/2007 | Neeper et al. | |
| 2010/0126286 A1* | 5/2010 | Self ......................... | G01N 35/04 73/863.81 |
| 2012/0060514 A1* | 3/2012 | Warhurst ................ | F25D 13/04 62/3.6 |
| 2012/0283867 A1 | 11/2012 | Gelbman et al. | |
| 2014/0305227 A1 | 10/2014 | Johns | |

OTHER PUBLICATIONS

International Search Report, International Application No. PCT/US2015/019126, dated May 27, 2015.

* cited by examiner

*Primary Examiner* — Kyle O Logan
(74) *Attorney, Agent, or Firm* — Perman & Green, LLP; Colin C. Durham

(57) ABSTRACT

An apparatus includes a frame configured to hold sample holders in an array, a longitudinal axis of the sample holder extending outward of an array plane; a drive section connected to the frame; at least one transfer arm rotatably connected to the drive section so that each transfer arm rotates about a rotation axis oriented substantially parallel with the longitudinal axis and includes a sample holder gripper; and at least one push member movably connected to the drive section and being distinct from the sample holder gripper and configured for linear movement along the longitudinal axis, the at least one push member being configured so that engagement with at least a bottom or top surface of the sample holder effects longitudinal translation of the sample holder for one or more of capture and release of the sample holder by the respective transfer arm in the longitudinal direction.

21 Claims, 18 Drawing Sheets

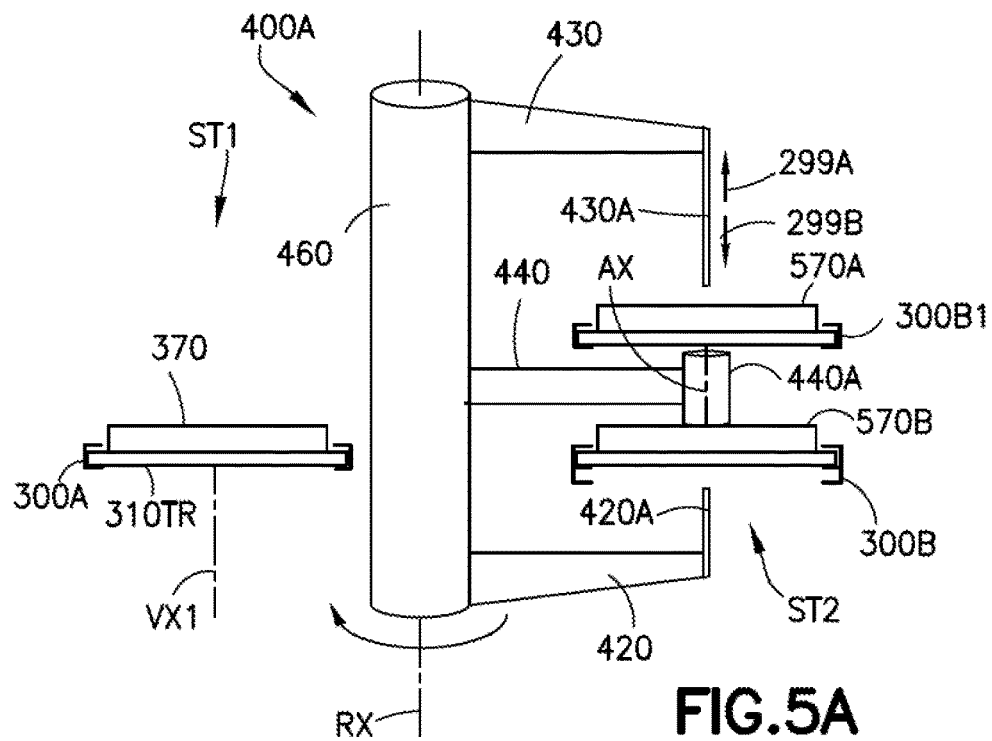
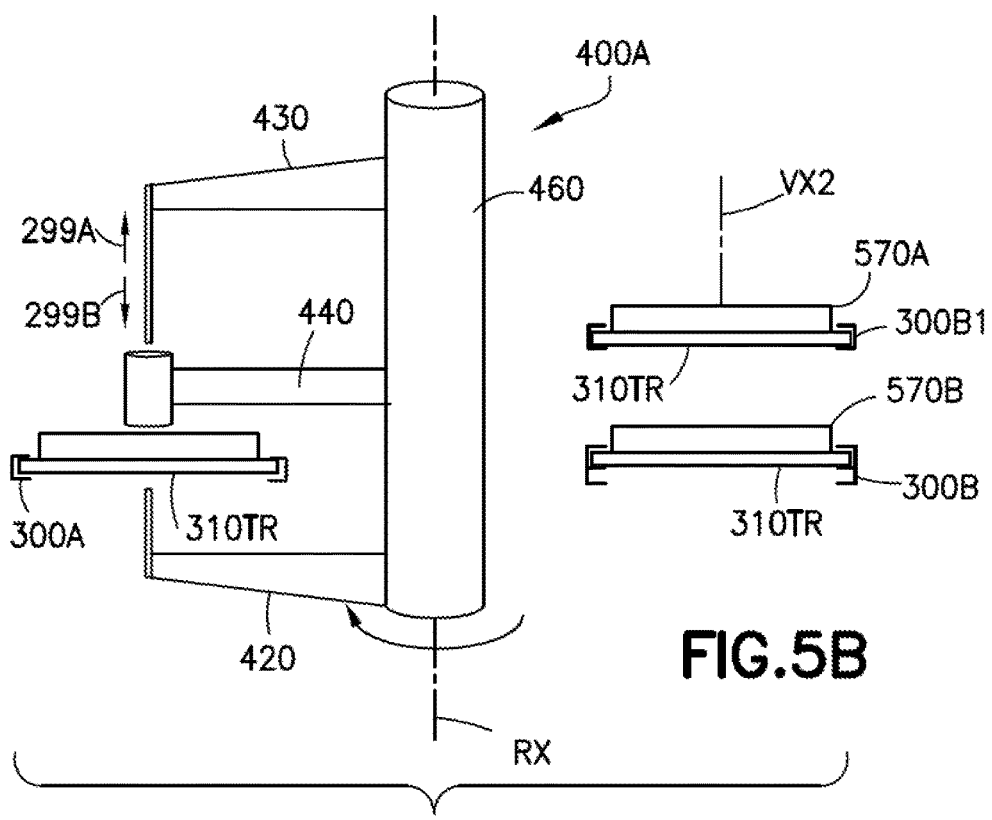

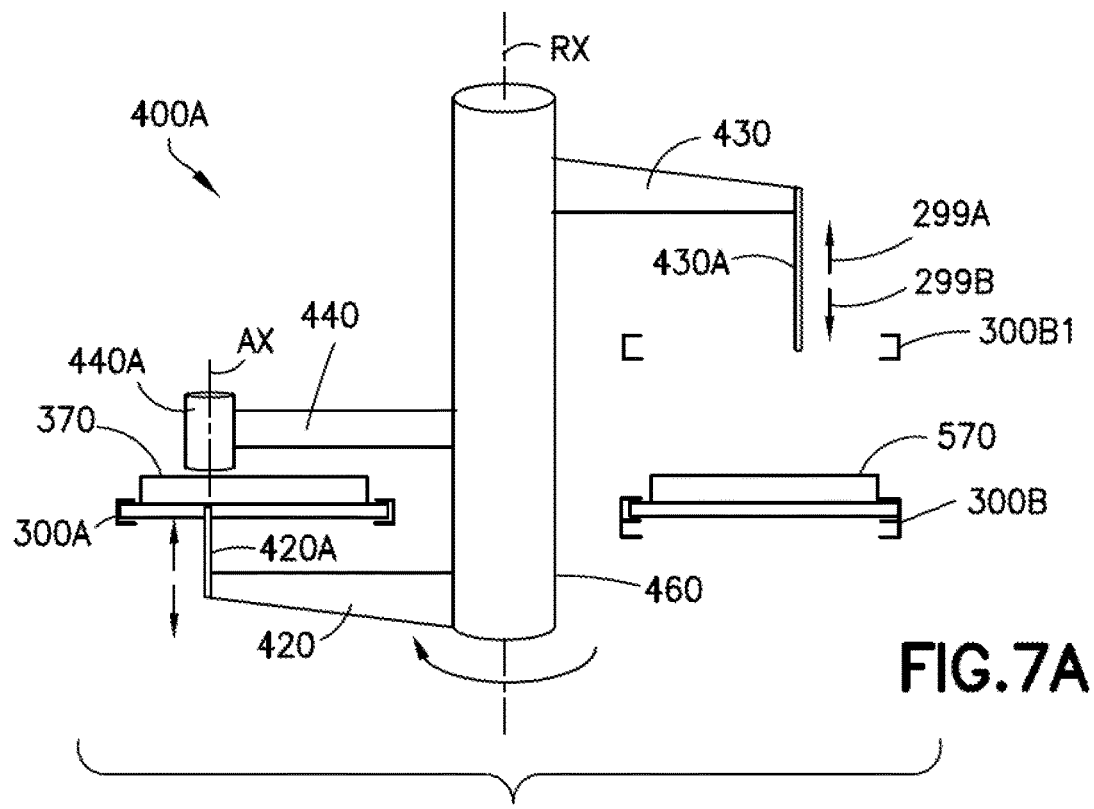
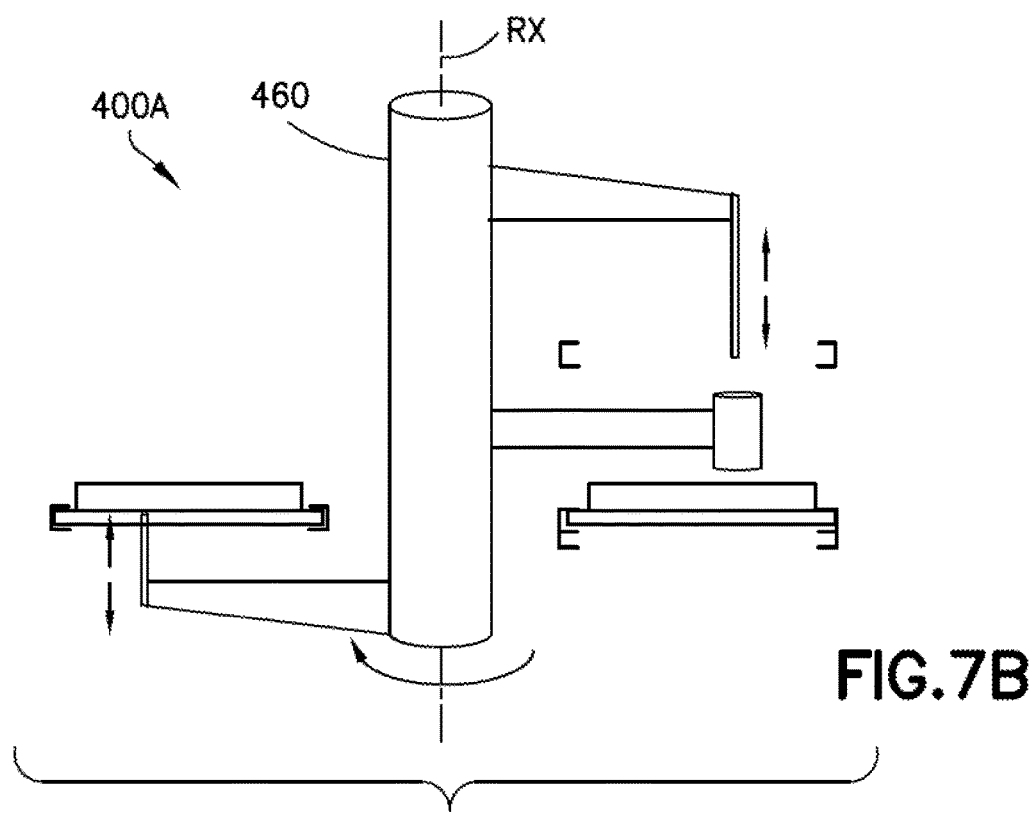

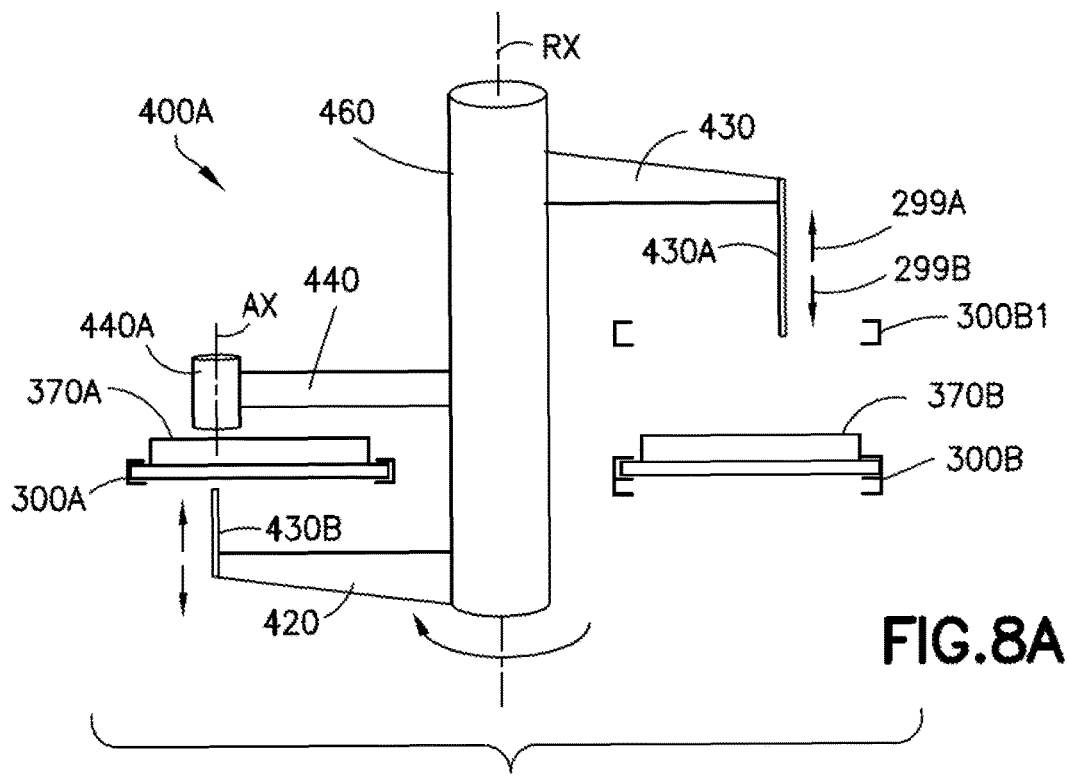
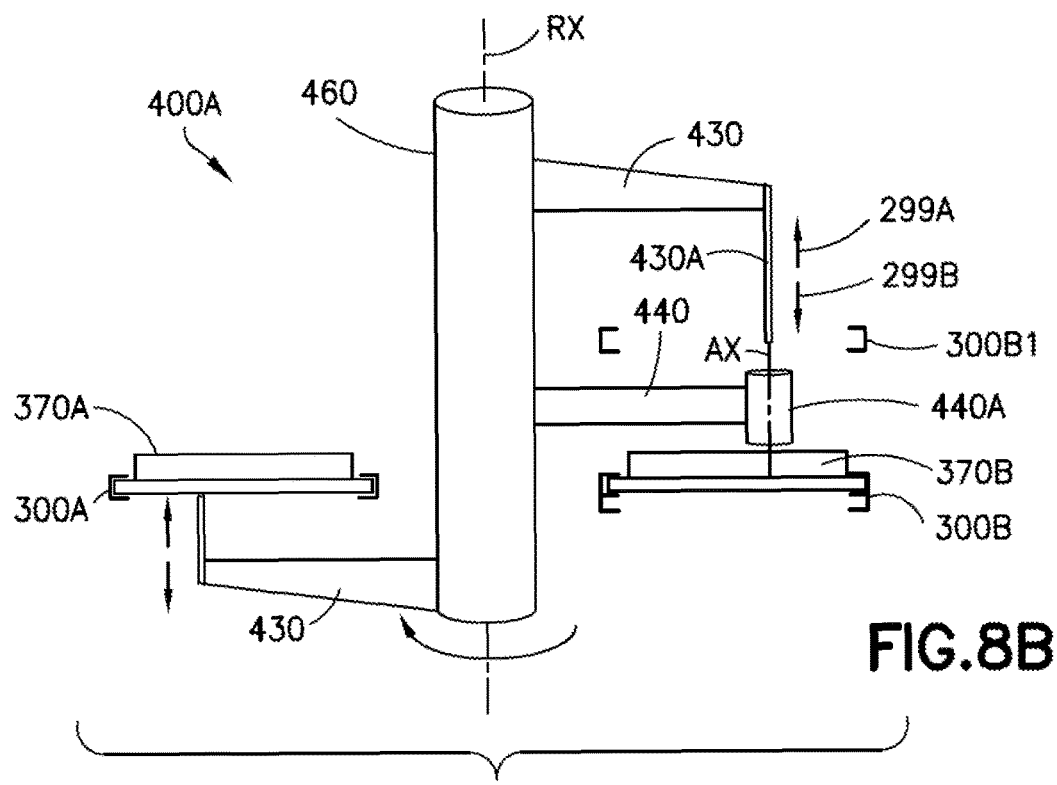

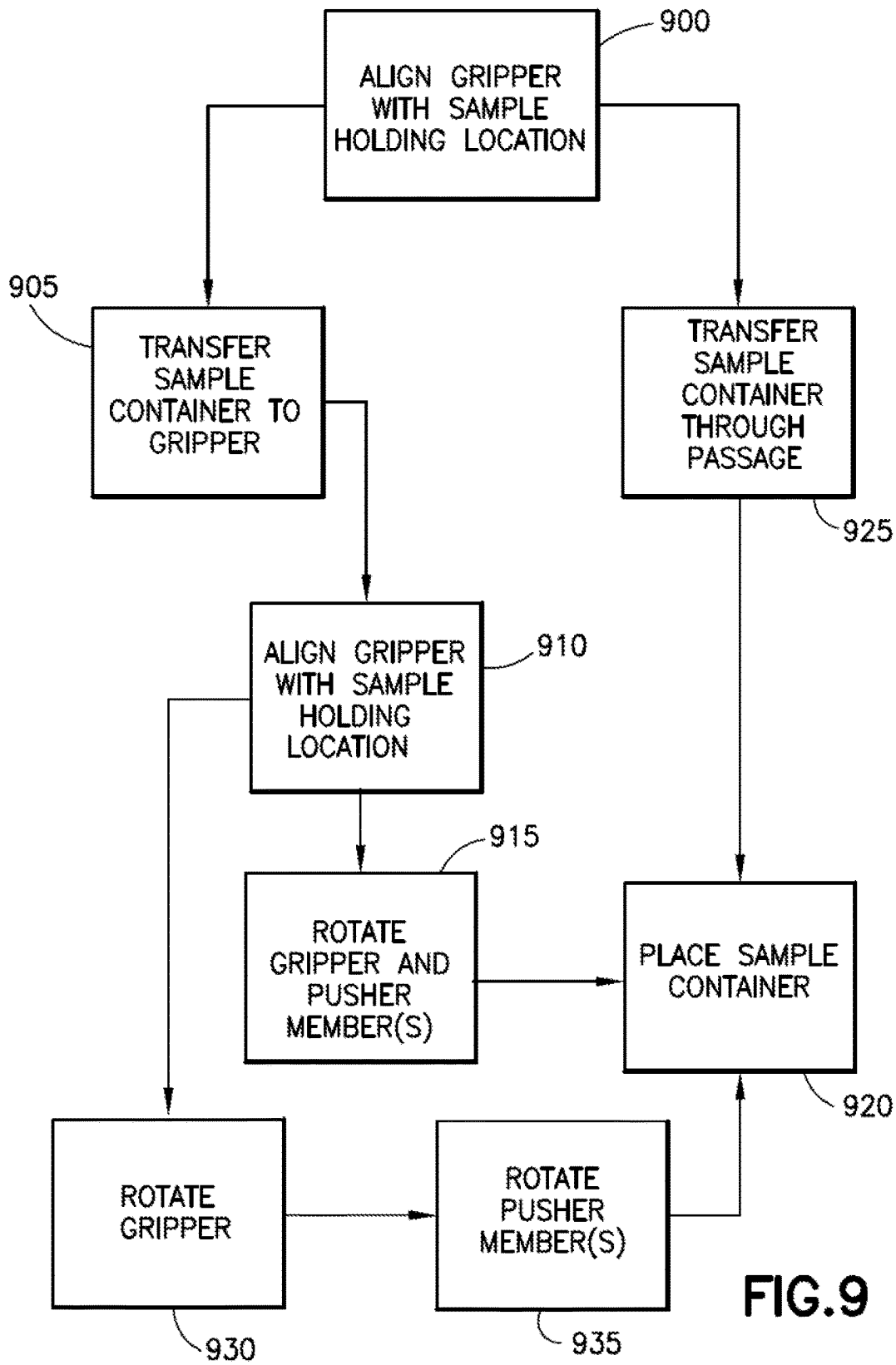

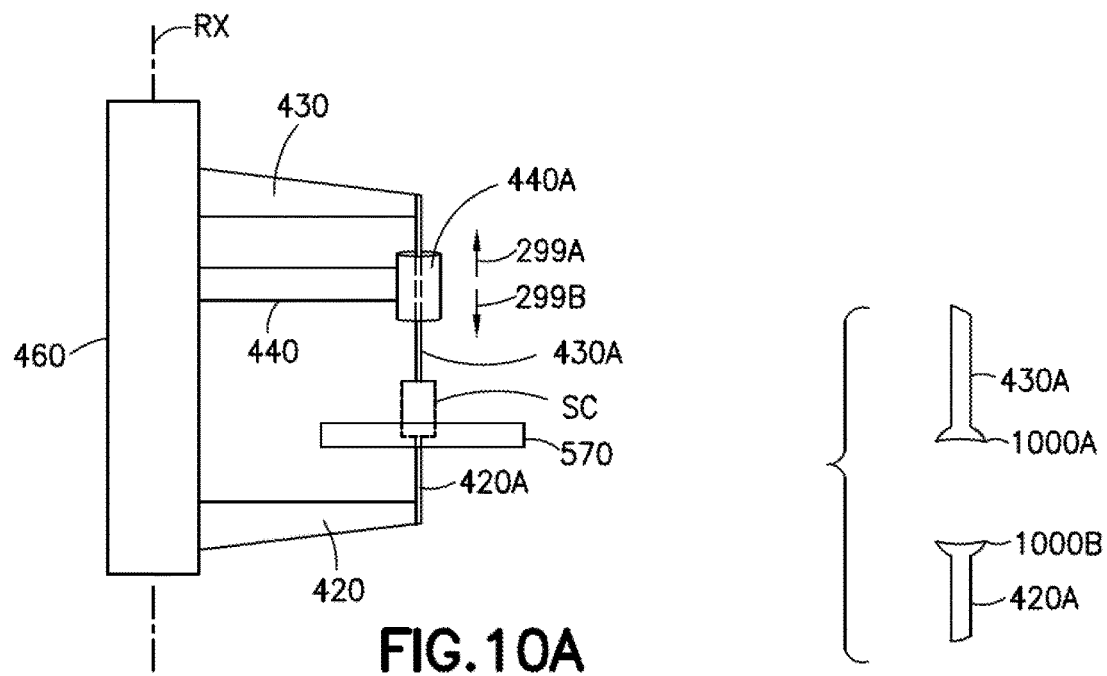
FIG.10A
FIG.10C
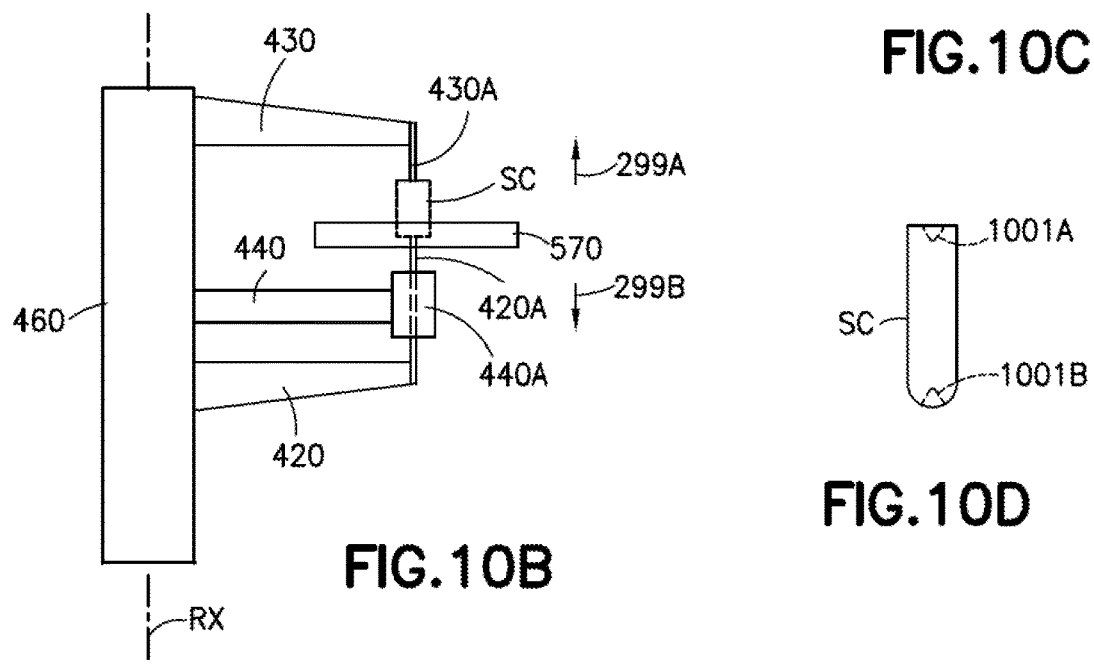
FIG.10B
FIG.10D

SAMPLE SELECTOR

CROSS-REFERENCE TO RELATED APPLICATIONS

This application is a division of U.S. patent application Ser. No. 14/229,077 filed on Mar. 28, 2014 (now U.S. Pat. No. 9,630,775), the disclosure of which is incorporated by reference herein in its entirety.

BACKGROUND

1. Field

The exemplary embodiments generally relate to sample picking mechanisms and, more particularly, to sample picking mechanisms for use within storage and retrieval systems used to store and retrieve samples.

2. Brief Description of Related Developments

Storage of samples, such as biological or chemical samples, may be stored at or below freezing temperatures. Generally the samples are stored at ultra-low temperatures ranging, for example, between about −50° C. to about −90° C. or at cryogenic temperatures ranging, for example, between about −140° C. to about −196° C. As used herein the term "ultra-low temperature" shall mean temperatures below −50° C. and above temperatures generally considered to be cryogenic.

Generally a mechanical robot is used to place and retrieve samples from the ultra-low temperature sample storage environment. However, the ultra-low temperature environment may be too cold for reliable operation of conventional sample picking mechanisms.

It would be advantageous to have a sample picking mechanism that is operable in ultra-low temperature environments where the drive(s) of the sample picking mechanism is (are) isolated from the ultra-low temperature environments.

BRIEF DESCRIPTION OF THE DRAWINGS

The foregoing aspects and other features of the disclosed embodiment are explained in the following description, taken in connection with the accompanying drawings, wherein:

FIGS. 5A and 5B are schematic illustrations of a portion of the sample selector of FIGS. 2A through 2D in accordance with aspects of the disclosed embodiment;

FIGS. 7A and 7B are schematic illustrations of a portion of the sample selector of FIGS. 2A through 2D in accordance with aspects of the disclosed embodiment;

FIGS. 8A and 8B are schematic illustrations of a portion of the sample selector of FIGS. 2A through 2D in accordance with aspects of the disclosed embodiment;

FIG. 9 is a flow diagram in accordance with aspects of the disclosed embodiment; and FIGS. 10A, 10B, 10C and 10D are schematic illustrations of a portion of the sample selector of FIGS. 2A through 2D in accordance with aspects of the disclosed embodiment.

DETAILED DESCRIPTION

Figure 1A:
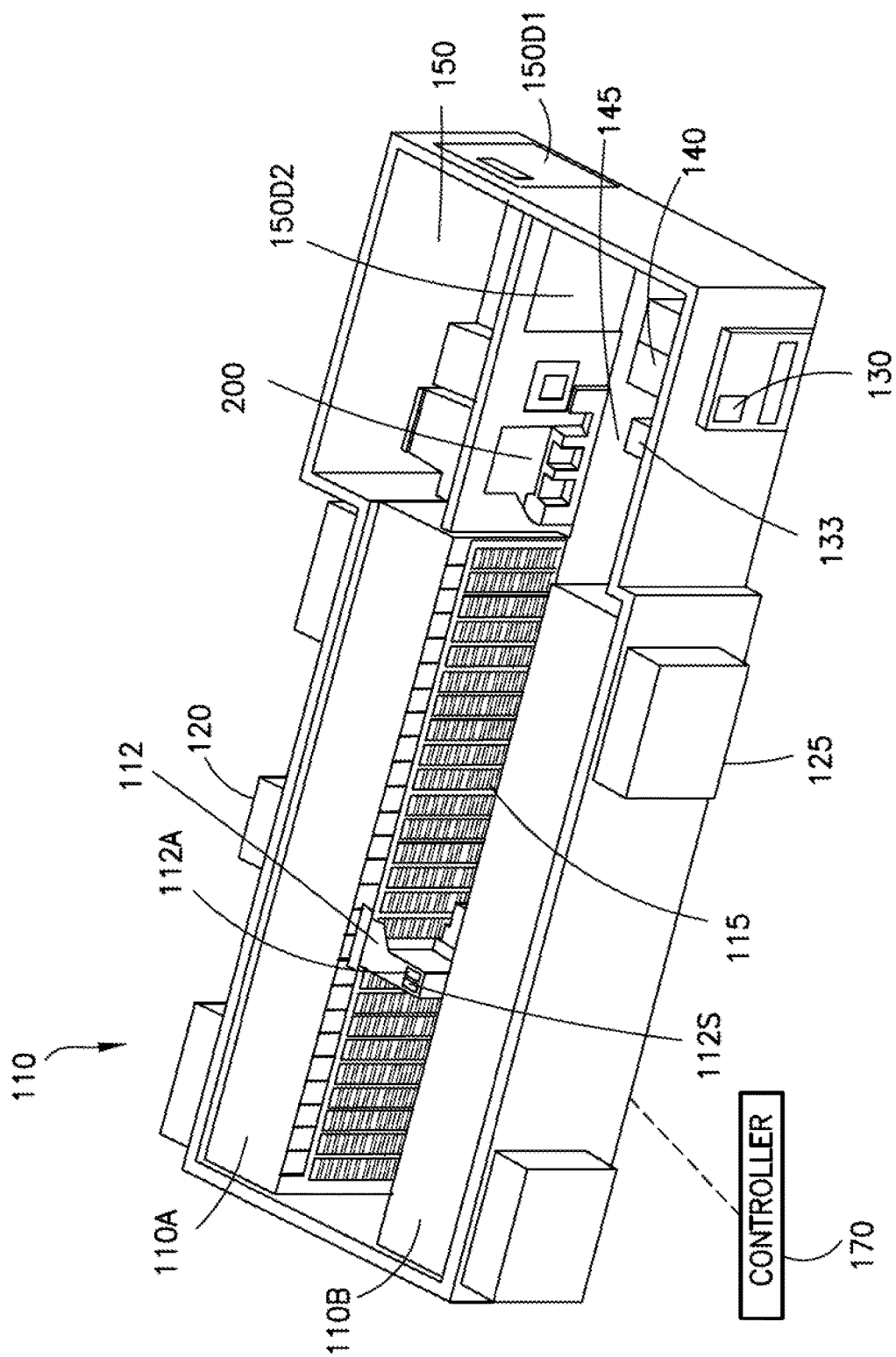
FIG. 1A is a schematic illustration of a sample storage facility in accordance with aspects of the disclosed embodiment.

FIG. 1A illustrates a sample storage facility or cold store 100 in accordance with aspects of the disclosed embodiment. Although the aspects of the disclosed embodiment will be described with reference to the drawings, it should be understood that the aspects of the disclosed embodiment can be embodied in many forms. In addition, any suitable size, shape or type of elements or materials could be used.

The sample storage facility 100 may include any suitable number of environmental zones or areas that may be isolated from one another. For example, the sample storage facility 100 may include one or more ultra-low temperature storage zones 110A, 110B, a transport zone 145 and a climate controlled antechamber 150. In other aspects the sample storage facility 100 may have any suitable number and type of zones/areas in which samples are stored and/or transported and which may be accessed by storage facility personnel.

In one aspect the transport zone 145 may include an input/output, module 130, a transport shuttle 112 and one or more sample selector modules 200 where the sample selector modules are disposed at least partly within the transport zone 145 as will be described below. The input/output module 130 may allow transfer of samples and/or sample trays to and from the sample storage facility 100 while maintaining a predetermined temperature within the transport zone 145. The sample selector modules 200, which will be described in greater detail below, may provide sorting capability for moving samples/sample holders within or between standard density (SD) and/or high density (HD) sample racks/trays.

The transport zone 145 may be maintained at any suitable low temperature, such as about −20° C., in which a transport shuttle 112 and/or other automation may operate to transfer sample trays between the ultra-low temperature storage zones 110A, 110B, the sample selector modules 200 and the input/output module 130. The transport shuttle 112 may interface with a tile wall 115 where each tile is arranged to create, for example, a robotically friendly insulating closure of the ultra-low temperature zones 110A, 110B for removing sample trays from the ultra-low temperature zones 110A, 110B in any suitable manner. The transport shuttle 112 may be configured to transport the sample trays between the ultra-low temperature zones 110A, 110B and any other components of the sample storage facility as described herein, which may include but is not limited to transport of sample trays to and from the sample selector modules 200.

In one aspect the climate controlled antechamber 150 may include doors 150D1, 150D2 for providing personnel access to the at least the transport zone 145 and/or to the sample selector modules 200, at least part of which may be disposed within the climate controlled antechamber 150 (e.g. the sample selector modules 200 may be mounted through a wall separating/isolating the antechamber 150 from the transport zone 145. As may be realized, the climate controlled antechamber 150 may be maintained at any suitable temperature allowing for human entry into the antechamber 150.

The sample storage facility 100 may include any suitable refrigeration system(s) 125 and/or dehumidification system(s) 120 for maintaining respective predetermined temperatures within the different zones of the sample storage facility 100. In one aspect the transport zone 145, transport shuttle 112, tile wall 115, ultra-low temperature storage zones 110A, 110B, transport zone 145 and input/output modules of the sample storage facility 100 may be substantially similar to those described in U.S. Pat. No. 7,635,246 issued on Dec. 22, 2009, U.S. Pat. No. 7,648,321 issued on Jan. 19, 2010, U.S. Pat. No. 7,793,842 issued on Sep. 14, 2010, U.S. Pat. No. 8,252,232 issued on Aug. 28, 2012 and U.S. patent application Ser. No. 13/595,817 filed on Aug. 27, 2012 and Ser. No. 13/334,619 filed on Dec. 22, 2011, the disclosures of which are incorporated by reference herein in their entireties.

Figure 1B:
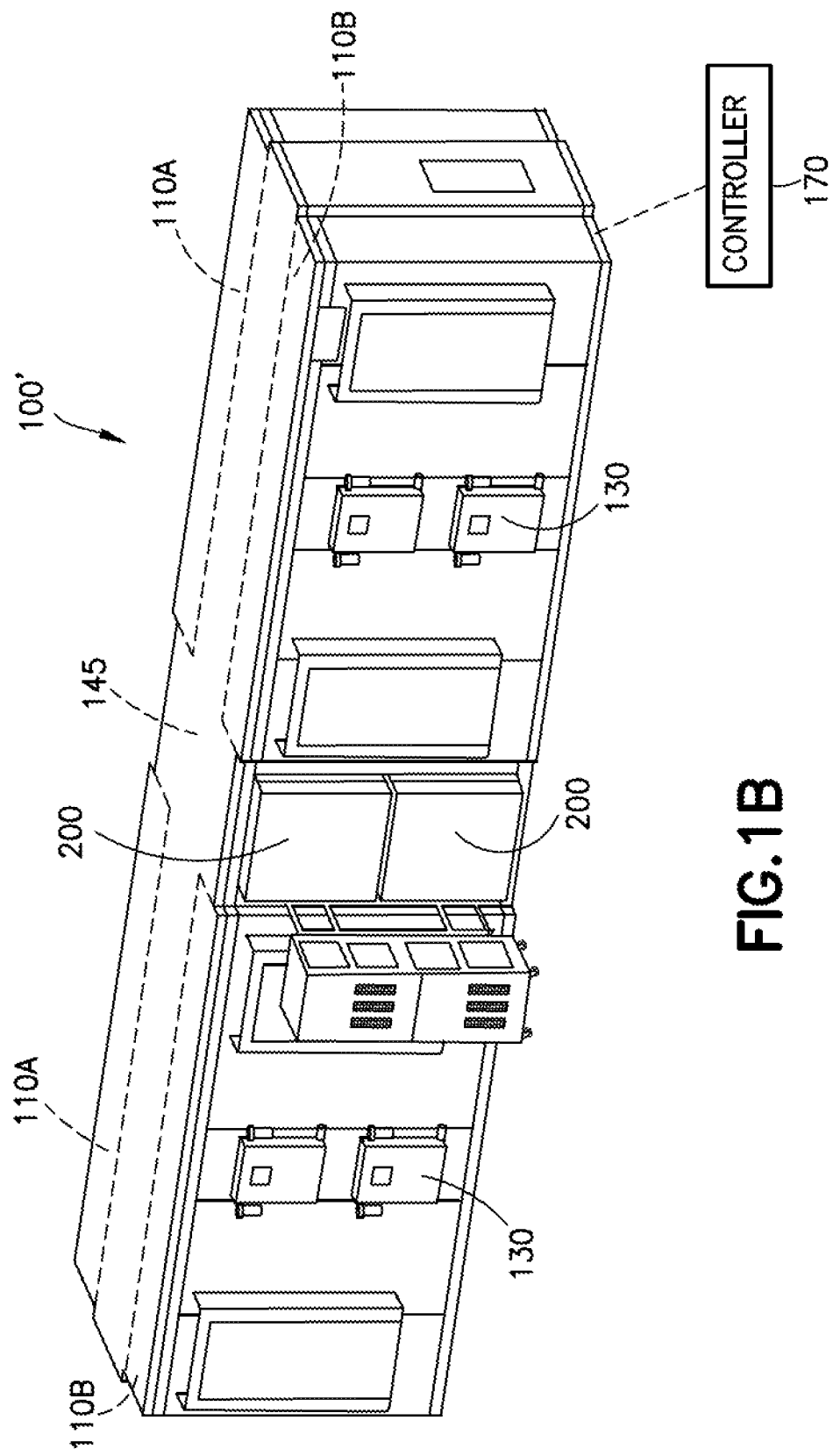
FIG. 1B is a schematic illustration of a sample storage facility in accordance with aspects of the disclosed embodiment.

FIG. 1B illustrates a sample storage facility 100' in accordance with aspects of the disclosed embodiment. The sample storage facility 100' may be substantially similar to sample storage facility 100 described above and include any suitable number of environmental zones or areas 110A, 110B, 145 that may be isolated from one another. Here one or more sample selector modules 200 may be mounted through an exterior wall of the sample storage facility 100' rather than through a wall separating/isolating the antechamber 150 from the transport zone 145 or any other suitable zone of the sample storage facility 100.

Figure 1C:
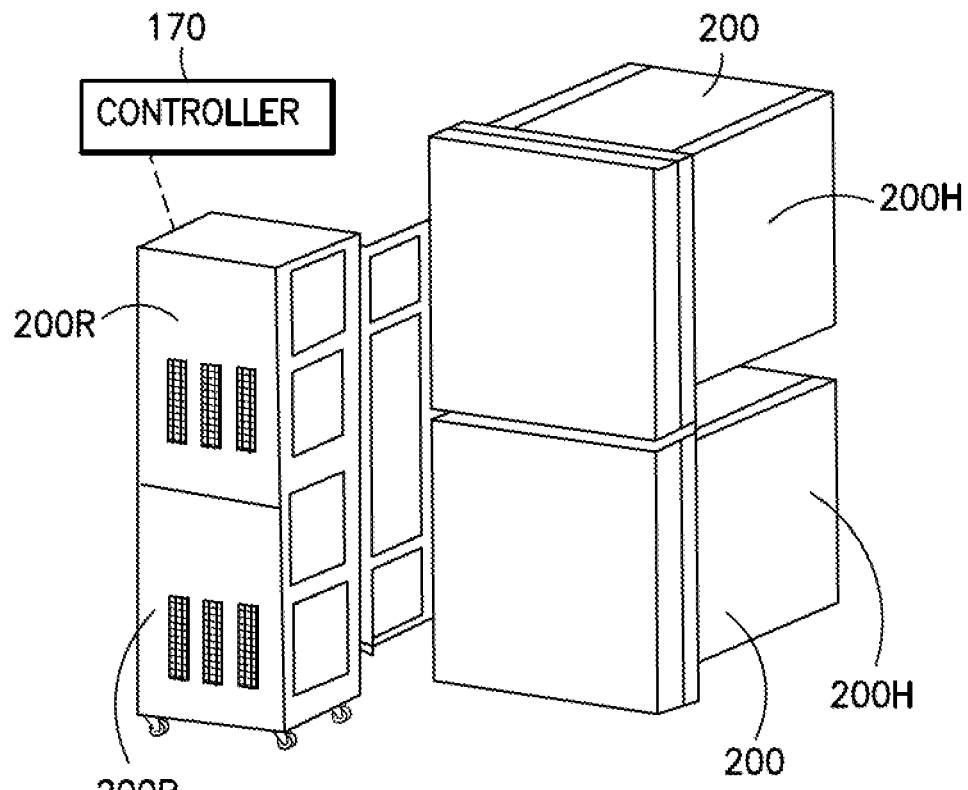
FIG. 1C is a schematic illustration of a sample selector module(s) in accordance with aspects of the disclosed embodiment.

FIG. 1C is a schematic illustration of sample selector modules 200. As may be realized, any suitable number of sample selector modules (two are shown in FIG. 1C) may be stacked one above the other as shown in FIGS. 1B and 1C or disposed side by side as illustrated in FIG. 1A. Each sample selector module 200 may be connected to or otherwise include any suitable refrigeration system 200R configured to maintain at least a portion of an interior of the sample selector at a predetermined ultra-low temperature as will be described below. In one aspect each sample selector module 200 may have a respective refrigeration system 200R while in other aspects a common refrigeration system may be provided for two or more sample selector modules 200 or the sample selector module(s) may share a common refrigeration system with other components (such as ultra-low temperature storage zones 110A, 110B) of the sample storage facility 100, 100'.

Figure 1D:
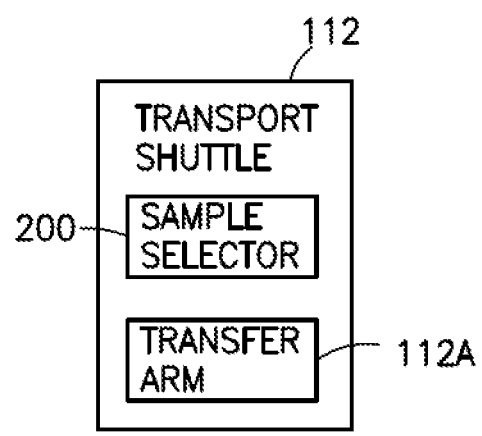
FIG. 1D is a schematic illustration of a sample selector module in accordance with aspects of the disclosed embodiment.
Figure 2A:
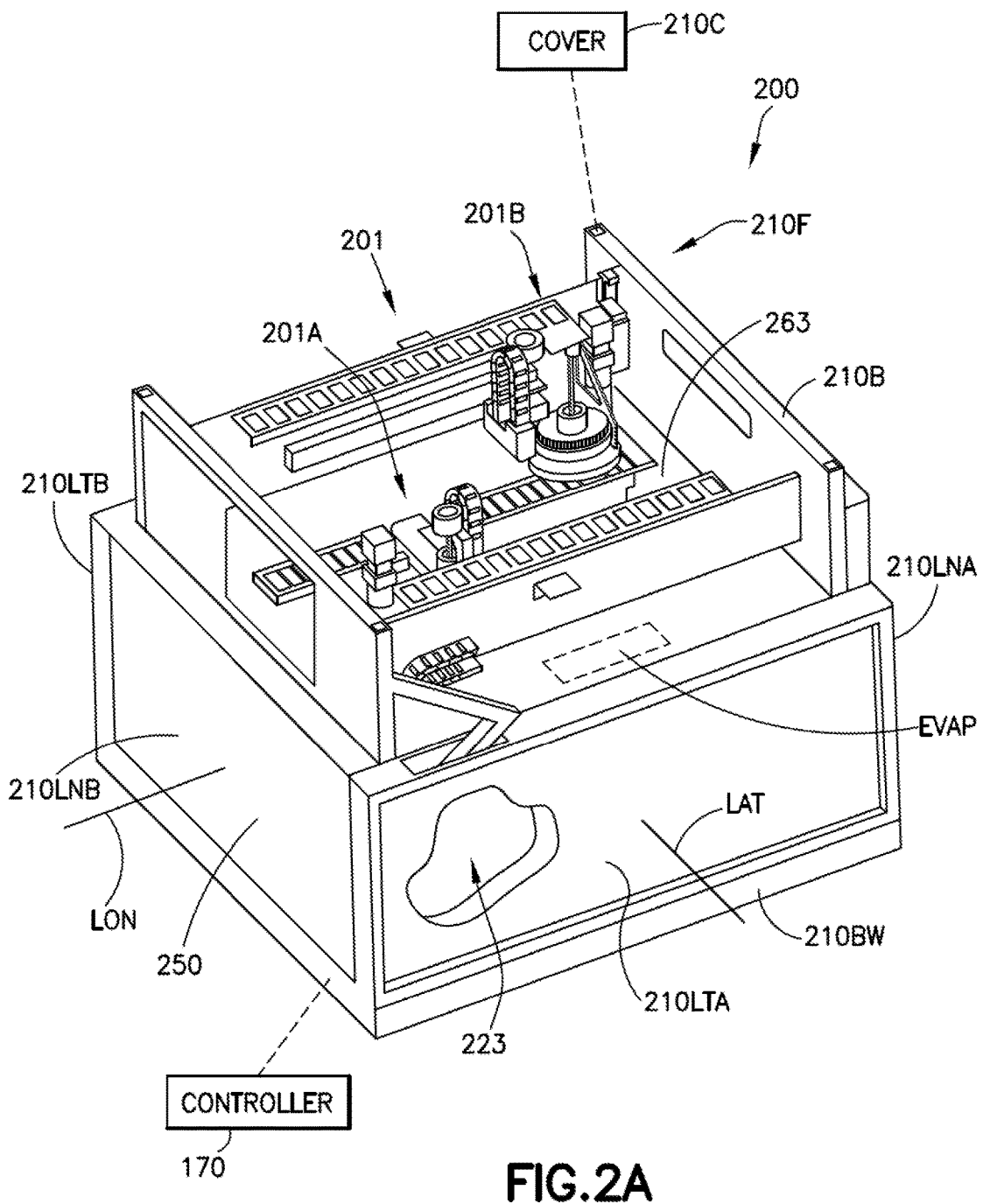
FIGS. 2A and 2B are schematic perspective illustrations of a portion of a sample selector in accordance with aspects of the disclosed embodiment.
Figure 2B:
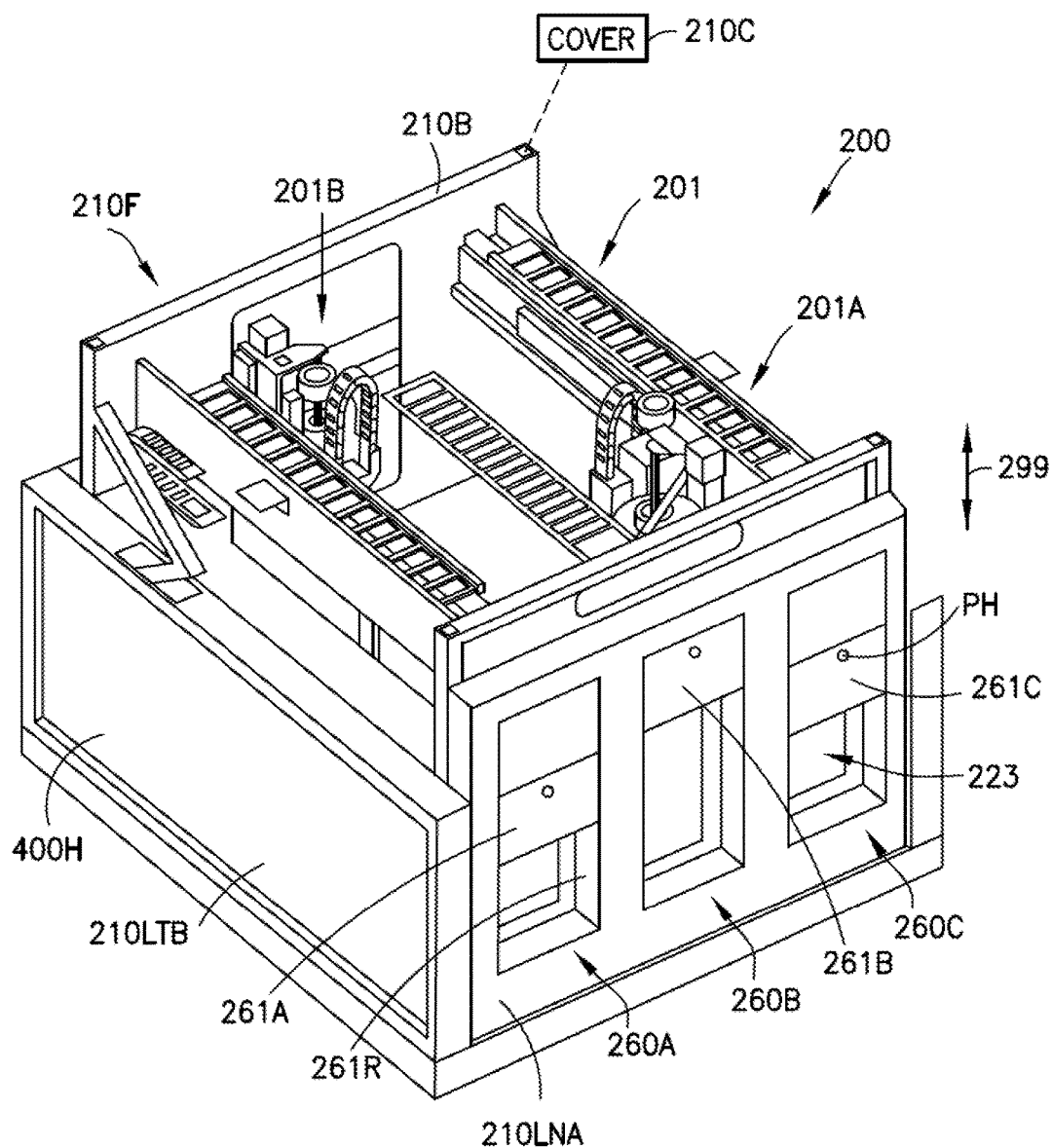
Figure 2C:
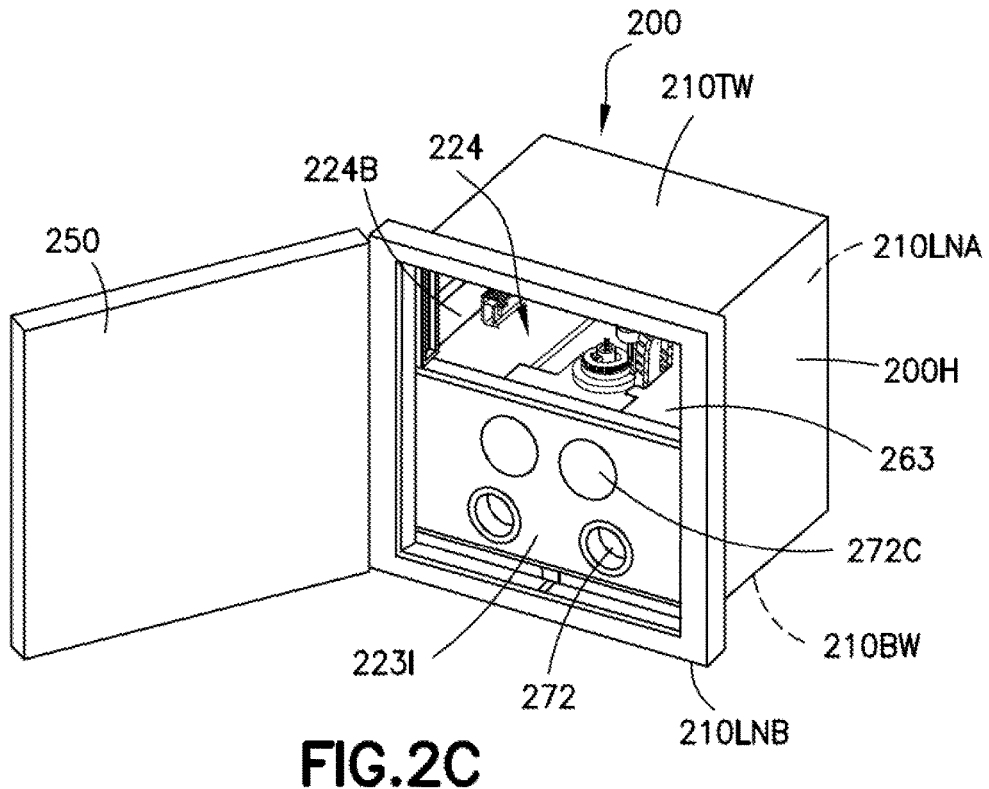
FIG. 2C is a schematic perspective illustration of the sample selector of FIGS. 2A and 2B in accordance with aspects of the disclosed embodiment.
Figure 2D:
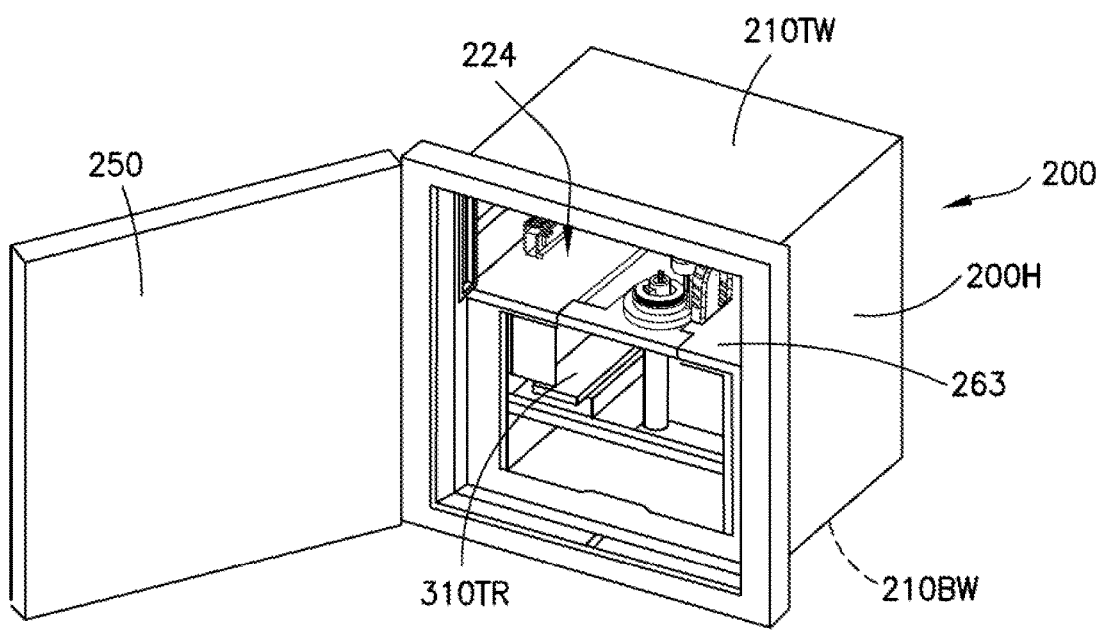
FIG. 2D is schematic perspective illustration of a portion of the sample selector of FIGS. 2A and 2B in accordance with aspects of the disclosed embodiment.

Referring also to FIG. 1D one or more sample selector modules 200 (and, in some instances, the respective refrigeration system 200R) may be mounted to, for example, the transport shuttle 112 so that the one or more sample selectors 200 move as a unit with transport shuttle 112. Here the transport shuttle 112 may include a transfer arm 112A configured to remove sample trays from the ultra-low temperature zones 110A, 110B (or any other suitable location of the sample storage facility 100, 100') and place the sample trays within the one or more sample selector modules 200 disposed on the transport shuttle 112. One or more samples from the samples frays may be sorted and/or transferred to a different tray, such as between source and destination trays, within the ultra-low temperature environment of the sample selector module 200 allowing the source tray to be placed back into the ultra-low temperature zone 110A, 110B. As may be realized, in aspects where the sample storage zone is the same temperature in which the transport shuttle 112 operates the sample selector 200 may not have a temperature controlled environment (e.g. such as the ultra-low temperature environment) but may be open to the transport shuttle operating environment.

Any suitable controller 170 may be connected to the sample storage facility 100, 100' in any suitable manner, such as through a wired or wireless connection. The controller 170 may be configured to control the operation of the sample storage facility 100, 100'. For example, the controller 170 may include any suitable memory and processors and be configured to track which samples are inserted and/or removed from the sample storage facility 100 and a location of each sample within the sample storage facility 100. The controller 170 may also be configured to control automation within the sample storage facility where the automation includes, but is not limited to, the transport shuttle 112 and sample selector modules 200 to transfer samples as described herein.

Referring now to FIGS. 2A, 2B, 2C and 2D each sample selector module 200 includes a frame 210F, at least one transfer device or unit 201A, 201B having a drive section 201 connected to the frame 210F and at least one transfer arm portion 400A (see FIGS. 4 and 4A) rotatably connected to the drive section 201. The frame 210F may include a cover portion 210C and a base portion 210B or include any suitable number of panels/walls (or a unitary/one piece panel) that form/forms a housing 200H configured to hold at least one isolated or sealed environment therein. The housing 200H may include a longitudinal axis LON and a lateral axis LAT and may be divided into isolated zones/areas. In one aspect the base portion 210B includes lateral walls 210LTA, 210LTB, longitudinal walls 210LNA, 210LNB, a bottom wall 210BW and an isolation member 263 disposed opposite to and spaced apart from the bottom wall 210BW (the term "bottom" is used herein for exemplary purposes only and in other aspects any suitable spatial identifiers may be associated with the wall 210BW) so as to form an isolated climate controlled chamber or zone 223. In one aspect the isolated climate controlled chamber 223 may be maintained at an ultra-low temperature, such as for example, about −80° C. or any other suitable ultra-low temperature. In one aspect the isolated climate controlled chamber 223 may be actively cooled while in other aspects the isolated climate controlled chamber 223 may be cooled in any suitable manner. One or more evaporators EVAP may be disposed within the isolated climate controlled chamber 223 and be configured to maintain, for example, a uniform ultra-cold temperature distribution within the isolated climate controlled chamber 223. In one aspect the one or more evaporators EVAP may be disposed on a surface of the isolation member 263 forming an interior wall of the isolated climate controlled chamber 223 (e.g. on a ceiling of the chamber). In other aspects the one or more evaporators EVAP may be disposed at any suitable location within the isolated climate controlled chamber 223, such as for example, on a surface of the walls 210LTA, 210LTB, 210LNA, 210LNB, 210BW that form an interior wall of the isolated climate controlled chamber 223. The one or more evaporators EVAP may be flat plate evaporators or any other suitable evaporator.

As may be realized, the isolation member 263 may also be disposed opposite to and spaced apart from a top wall 210TW (e.g. the isolation member is disposed between the top and bottom walls 210TW, 210BW) so as to form a drive section chamber 224 that may be maintained at any suitable predetermined temperature suitable for the operation of drive section 201 components as described herein. In one aspect, the drive section chamber 224 may be maintained at any suitable temperature above, for example, ultra-low temperatures such as a temperature of about −20° C.

At least one of the of the longitudinal walls 210LNA, 210LNB and the lateral walls 210LTA, 210LTB may include one or more input/output openings or apertures 260A, 260B, 260C through which sample trays 310TR pass for insertion to and removal from the isolated climate controlled zone 223. Each input/output opening 260A, 260B, 260C may be a sealable or otherwise closable opening that is sealed or otherwise closed by a respective sliding tile 261A, 261B, 261C. Suitable examples of sliding tile closures can be found in, for example, U.S. Pat. Nos. 7,635,246; 7,648,321 and 7,793,842; and U.S. patent application Ser. Nos. 13/595,817 and 13/334,619, previously incorporated by reference herein. In one aspect the tiles 261A, 261B, 261C may be foam bricks or blocks that are arranged to create, for example, a robotically friendly insulating closure. In other aspects, the tiles 261A, 261B, 261C may be constructed of any suitable material and may interface with any suitable automation and/or personnel for opening and closing a respective input/output opening 260A, 260B, 260C in any suitable manner. In one aspect, the tiles 261A, 261B, 261C may be held in place (e.g. in a closed position) by gravity or in any other suitable manner. Guide rails 262R on each side of a respective tile may constrain the tiles against lateral movement while allowing them to slide up and down freely in the direction of arrow 299 for opening and closing a respective input/output opening 260A, 260B, 260C. In one aspect, any suitable automated transfer mechanism of the sample storage facility 100, such as transport shuttle 112, may insert or remove a sample tray 310TR to or from the isolated climate controlled zone 223 through an input/output opening 260A, 260B, 260C by aligning the automated transfer mechanism with the tile 261A, 261B, 261C in front of the desired opening. Each tile 261A, 261B, 261C may be configured with one or more gripping members PH, such as a recess or protrusion, that allows the automated transfer mechanism to lift the tile 261A, 261B, 261C for opening the input/output opening 260A, 260B, 260C in, for example, a manner substantially similar to that described in U.S. Pat. Nos. 7,635,246; 7,648,321 and 7,793,842; and U.S. patent application Ser. Nos. 13/595,817 and 13/334,619, previously incorporated by reference herein. In other aspects the sample selector module 200 may include one or more drives coupled to each of the tiles 261A, 261B, 261C for moving the tiles in the direction of arrow 299 to open and close a respective input/output opening 260A, 260B, 260C.

As may be realized, each tile 261A, 261B, 261C may form any suitable seal with the respective wall 210LNA, 210LNB, 210LTA, 210LTB. In one aspect the seal may be a selectively activated magnetic seal that may be activated when the tiles 261A, 261B, 261C are in a closed position. The magnetic seal may be deactivated to allow movement of the tiles 261A, 261B, 261C in the direction of arrow 299 for opening and closing the respective input/output opening 260A, 260B, 260C. In other aspects the magnetic seal may be a passive seal where the robot, other automation or a user is able to overcome a sealing force provided by the passive magnetic seal for moving the tiles 261A, 261B, 261C in the direction of arrow 299 for opening and closing the respective input/output opening 260A, 260B, 260C. For example, the magnetic seal may be provided by any suitable magnet having, for example, high normal forces and lower shear forces such as neodymium magnets so that the respective tile 261A, 261B, 261C is held or otherwise biased against the wall while being able to move relative to the respective input/output opening 260A, 260B, 260C for opening and closing the respective input/output opening 260A, 260B, 260C. It is noted that the tiles, such as tiles 261A, 261B, 261C, may be disposed on any suitable enclosure 133 that is accessed by the transport shuttle 112 or any other suitable transport of the sample storage facility 100, 100'. In one aspect the enclosure 133 may be an enclosure for one or more of a sample picking module a bar code reader, an input output module, a storage module or any other suitable device that interfaces with one or more sample containers.

Figure 3A:
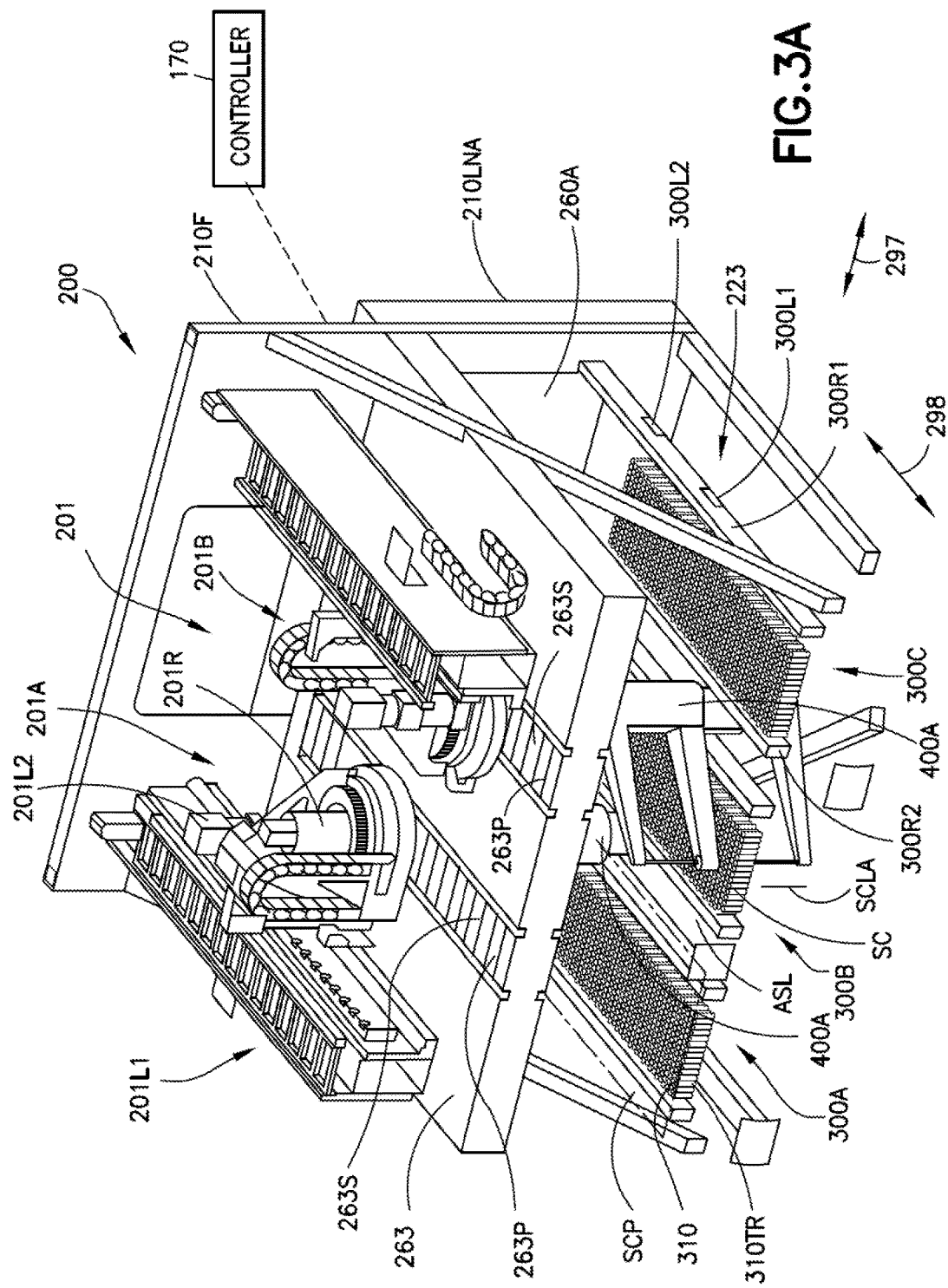
FIG. 3A is a schematic perspective illustration of a portion of the sample selector of FIGS. 2A through 2D in accordance with aspects of the disclosed embodiment.
Figure 3B:
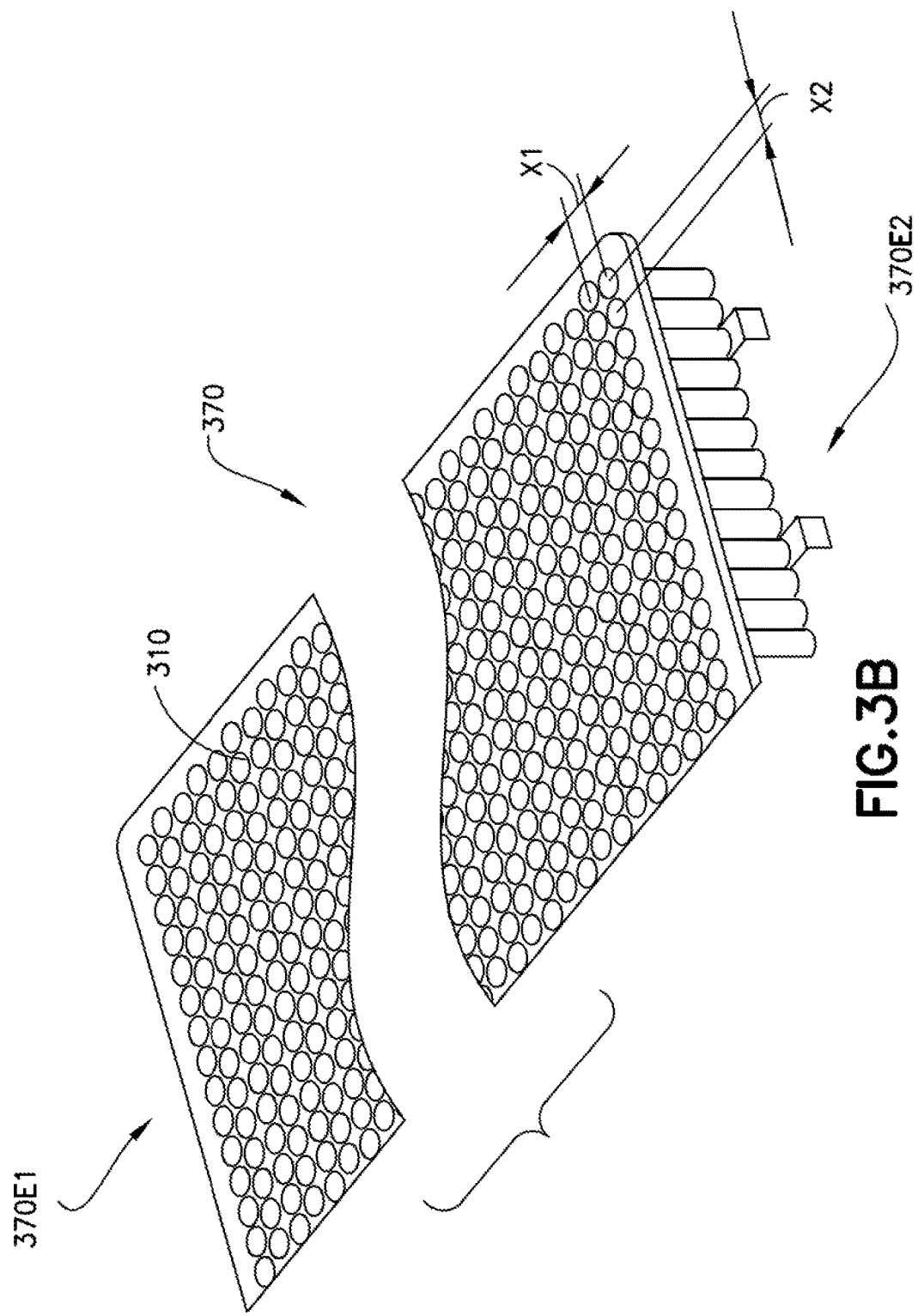
FIG. 3B is a schematic illustration of a portion of a sample tray in accordance with aspects of the disclosed embodiment.

Referring also to FIG. 3A, each of the input/output openings 260A, 260B, 260C may be associated with a respective sample tray holder 300A, 300B, 300C. Each sample tray holder 300A, 300B, 300C may include respective sample tray supports 300R1, 300R2 that may be supported by the frame 210F in any suitable manner. While a single level or plane of sample tray holders is illustrated in FIG. 3A, in other aspects there may be multiple stacked levels or planes of sample tray holders within the isolated climate controlled zone 223 (as will be described below) between which sample containers may be transferred. The sample tray supports 300R1, 300R2 may be spaced from each other by any suitable amount so that a sample tray 310TR may be slid into or out of the respective sample tray holder 300A, 300B, 300C by a tray conveyor that is external to the sample selector module 200 (e.g. the tray conveyor is one that is separate from the sample selector module 200 such as the tray shuttle 112). In one aspect, each sample tray holder 300A, 300B, 300C may have a length suitable for holding a sample tray 310TR having one or more standard density or high density sample racks (see the high density sample racks generally referred to as high density racks 370 in FIG. 3B and the standard density sample racks generally referred to as standard density racks 570 in FIGS. 5A-7B which will be described in greater detail below) disposed thereon such that, the sample racks are arranged end to end (e.g. referring to FIGS. 3B and 3C for exemplary purposes only, a first end of a sample racks 370E1 substantially abuts against a second end 370E2 of another sample rack 370). In other aspects the sample tray 310TR may be configured to hold samples container directly thereon (e.g. without a tray) such that the sample container holding locations 310 are formed in the sample tray 310TR or are otherwise affixed thereto in a standard density or high density capacity. The sample trays 310TR (and/or the racks 370, 570 held thereon) may be configured to hold sample containers of holder SC in an array of sample containers, where the array has an array plane SCP. The sample containers SC may be arranged in the sample trays 310TR (and/or the racks 370, 570 held thereon) so that a longitudinal axis SCLA of the sample containers SC extends outward of the array plane. In one aspect each sample tray holder 300A, 300B, 300C may include a retention unit 300L1 and/or locating unit 300L2 for securely holding and locating the sample tray(s) 310TR within the sample tray holder(s) 300A, 300B, 300C in a repeatable manner so as to place each sample holding location 310 of the sample racks in a predetermined position relative to a coordinate system of the sample picker module 200.

Referring also to FIG. 1A, in one aspect, a sample tray 310TR may be inserted into the sample selector module 200 by positioning the sample tray on a tray support surface 112S of the transport shuttle 112. The sample tray 310TR may be positioned by the tray shuttle 112 at a height corresponding to a predetermined input/output opening 260A, 260B, 260C. The transport shuttle 112 may slide a predetermined tile 261A, 261B, 261C to open an associated input/output opening 260A, 260B, 260C in any suitable manner, such as that described above. The transport shuttle may slide the sample tray 310TR into the sample tray holder 300A, 300B, 300C associated with the predetermined input/output opening 260A, 260B, 260C using, for example, a transfer arm 112A of the transport shuttle 112. In one aspect the sample tray may include any suitable gripping feature that allows the transport shuttle 112 to grip the sample tray 300TR for sliding the sample tray to and from the sample tray holder 300A, 300B, 300C. The transfer arm 112A may be removed from the sample selector module 200 and the tile may be moved to close or otherwise seal the input/output opening 260A, 260B, 260C. Removal of the sample tray 300TR may be performed in substantially the opposite manner to that described above.

Referring again to FIGS. 2C and 2D, another one of the longitudinal walls 210LNA, 210LNB and/or the lateral walls 210LTA, 210LTB may include a user access door 250 configured to allow a user access to one or more of the drive section chamber 224 and the isolated climate controlled chamber 223. Opening or removal of the door 250 may provide substantially direct user access to the drive section chamber 224. In one aspect any suitable barrier member 224B may be connected to the frame 210F to form, for example, a removable moisture barrier between the drive section chamber 224 and the user environment. In one aspect the barrier member 224B may be a translucent member allowing visual inspection of the drive section chamber 224 without removal of the barrier member 224B. Opening or removal of the door 250 may also provide access to the isolated climate controlled chamber 223. In one aspect opening the user access door 250 may provide substantially direct access to the isolated climate controlled chamber 223. In other aspects access to the isolated climate controlled chamber 223 may be provided through an ultra-cold temperature interface or thermal panel 223I. The ultra-cold temperature interface or thermal panel 223I may be coupled to the frame 210F so as to substantially seal or otherwise isolate the isolated climate controlled chamber 223 from the user environment when the door 250 is opened or removed. The ultra-cold temperature interface 223I may include one or more suitable sealable apertures 272 through which gloves may be inserted. In one aspect any suitable covers 272C may be provided for sealing the apertures 272 while in other aspects the gloves may be attached to the apertures to seal the apertures.

As may be realized, any suitable seals may be provided between the respective wall 210LNA, 210LNB, 210LTA, 210LTB and one or more of the user access door 250, barrier member 224B and ultra-cold temperature interface 223I. For example, where the user access door 250 provides direct access to one or more of the drive section chamber 224 and isolated climate controlled chamber 223, any suitable seals may be provided between the door 250 and walls 210LNA, 210LNB, 210LTA, 210LTB (and isolation member 263) for sealing or otherwise isolating one or more of the drive section chamber 224 and isolated climate controlled chamber 223 from each other and from an environment outside the sample selector module 200. In other aspects, the barrier member 224B may form a seal with the walls 210LNA, 210LNB, 210LTA, 210LTB (and isolation member 263) for sealing or otherwise isolating the drive section chamber 224. As noted above, the ultra-cold temperature interface 223I may be coupled to the frame 210F so as to substantially seal or otherwise isolate the isolated climate controlled chamber 223 from the user environment when the door 250 is open or removed. The seals between the respective wall 210LNA, 210LNB, 210LTA, 210LTB and one or more of the user access door 250, barrier member 224B and ultra-cold temperature interface 223I may be magnetic seals similar to those described above with respect to tiles 261A, 261B, 261C or they may be any suitable seals provided individually or in conjunction with each other.

Figure 4:
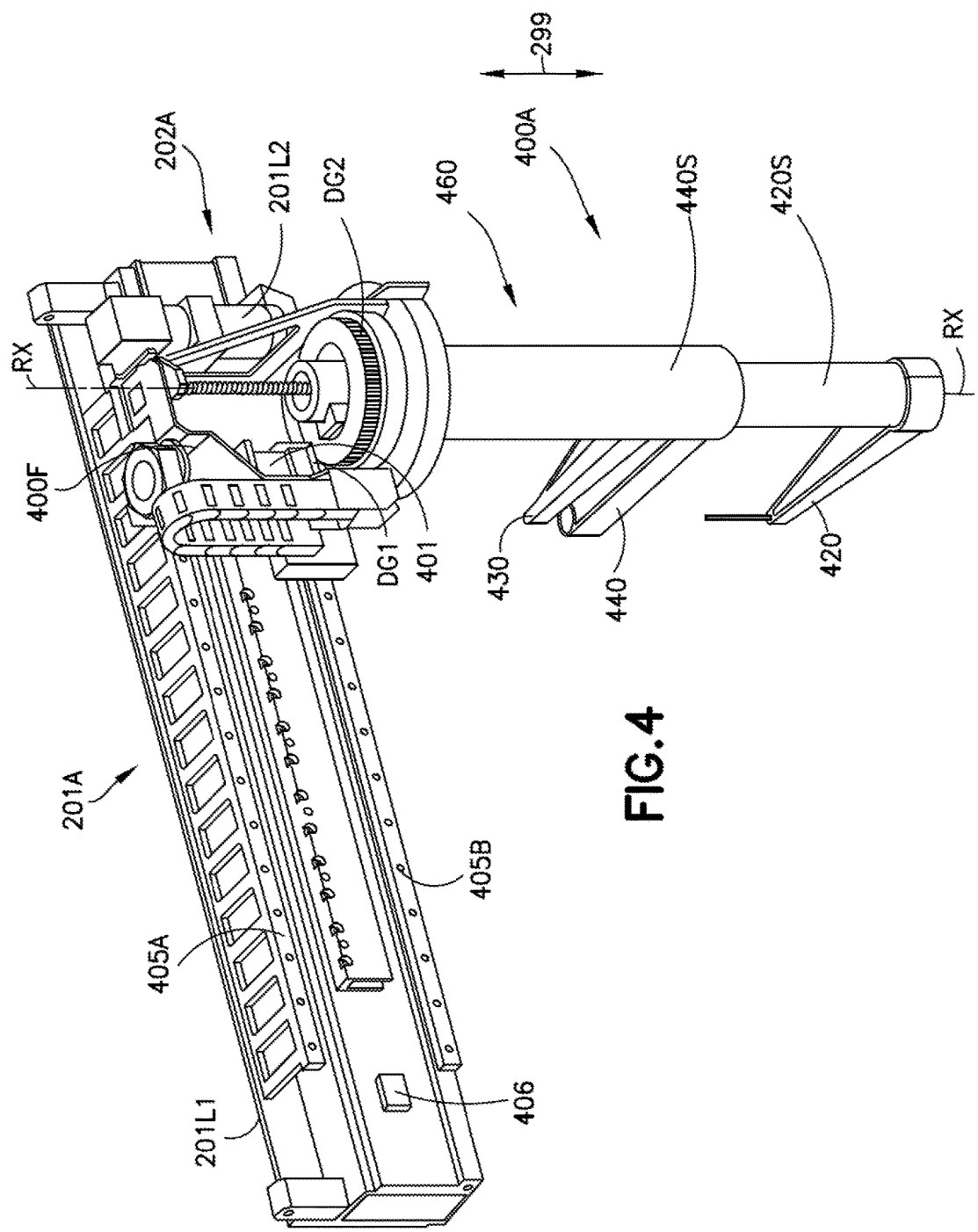
FIGS. 4, 4A, 4B, 4C, 4D and 4E are schematic illustrations of portions of the sample selector of FIGS. 2A through 2D in accordance with aspects of the disclosed embodiment.
Figure 4A:
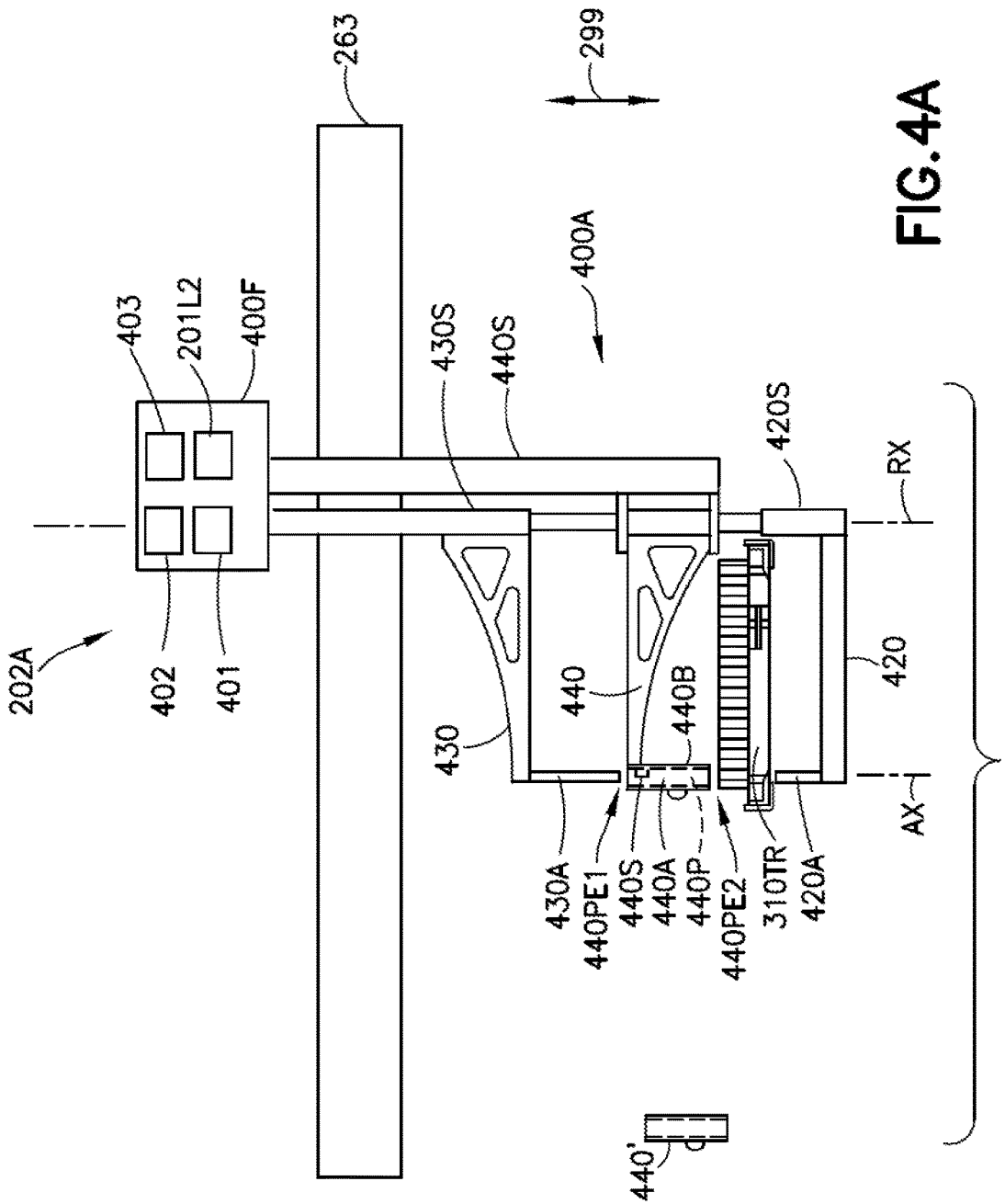

Referring now to FIGS. 3A, 4 and 4A, as noted above the sample transfer module 200 includes one or more transfer devices 201A, 201B. Each transfer device 201A, 201B (described herein with respect to transfer device 201A but it should be understood that transfer device 201B may be identical to transfer device 201A) includes a respective drive portion 202A of drive section 201 and a transfer arm portion 400A. The drive portion 202A may be disposed within the drive section chamber 224 and include one or more rotary drive motors 401, 402, 403 connected to a frame 400F of the drive portion 202A. In one aspect the drive portion 202A may also include at least one linear drive motor 201L2 connected to the frame 400F for moving at least a portion of the transfer arm portion 400A in the direction of arrow 299.

In one aspect, the drive portion 202A may be coupled to the frame 210F of the sample selector module 200 in any suitable manner. For example, the drive portion 202A may be mounted to a linear drive 201L1 of the drive section 201 that is supported within the frame 210F so that a path of travel of the linear drive 201L1 and movement of the transfer arm portion 400A carried by the linear drive 201L1 is substantially in the direction of arrow 298 (e.g. along a longitudinal axis of the sample tray 310TR or towards and away from the longitudinal walls 210LNA, 210LNB) so that the transfer arm portion travels along a respective aisle formed between the sample tray holders 300A, 300B, 300C. In other aspects the linear drive 201L1 may be a multi-axis linear drive providing movement of the transfer arm portion 400A in the direction of arrows 297, 298. The linear drive 201L1 may be any suitable linear drive such as a linear stepper motor, a belt and pulley system, a screw drive or any other suitable drive. In one aspect the drive portion 202A may ride along one or more linear rails 405A, 405B of the linear drive 201L1 while in other aspects the drive portion 202A may be supported by the linear drive 201L1 in any suitable manner. As may be realized, any suitable encoders or position detectors 406 may be provided for determining, along with controller 170, a position of the transfer arm portion 400A along a length of the linear drive 201L1 for positioning the transfer arm portion 400A relative to the sample holding locations 310 within the sample tray 310TR.

The transfer arm portion 400A may include a coaxial (e.g. concentrically collocated) drive shaft assembly 460 having a common axis of rotation RX (which may be substantially parallel with the sample container longitudinal axis SCLA), a sample container holder 440, a top (e.g. upper) pusher member 430 and a bottom (e.g. lower) pusher member 420. It is noted that the terms "top" and "bottom" make reference to an end or surface of a sample container that a sample container engagement portion 420A, 420B (described below) of the respective "pusher member" engages (e.g. the "top" surface SCT of the sample container SC includes an opening that is closed by a cap and the "bottom" surface SCB of the sample container includes a closed end of the sample container SC opposite the opening) and in other aspects any suitable spatial references/identifiers may be used. The coaxial drive shaft assembly 460 and other components of the transfer arm portion 400A may be constructed of any suitable material such as, for example, a thermally non-conductive material configured to isolate the samples held by the transfer arm portion 400A from heat generated by the drive portion 201A, 202A and to isolate the drive portion from the ultra-cold temperature in which the transfer arm portion 400A operates.

The coaxial drive shaft may be coupled to the respective drive portion 202A in any suitable manner (such as described below) and extend through the isolation member 263 into the isolated climate controlled chamber 223. In one aspect the isolated climate controlled chamber 223 may include one or more narrow slots 263P (e.g. a value of longitudinal length of the slot is much less than a value of the lateral width of the slot) through which a respective coaxial drive shaft assembly 460 extends. The narrow slots 263P may be decoupled from at least one degree of freedom of a respective transfer device 201A, 201B in the array plane SCP. The narrow slot 263P may be sealed in any suitable manner such as with a dynamic seal 263S that moves with the coaxial drive shaft assembly 460 as the coaxial drive shaft assembly 460 travels in the direction of arrow 298 along a longitudinal length of the respective narrow slot 263P. As may be realized, the decoupling of the narrow slot 263P from the at least one degree of freedom of the respective transfer device 201A, 201B may allow for seal movement in only a single direction, such as along a travel axis in the direction of arrow 298 of a respective transfer arm portion. In other aspects the narrow slot 263P may not be sealed where the isolation of the isolated climate controlled chamber 223 may be achieved by air currents flowing from the isolated climate controlled chamber 223 into the drive section chamber 224 due to, for example, a temperature differential between the two chambers, however the drive section chamber 224 may be maintained at a predetermined non-ultra-cold temperature in any suitable manner that accounts for cooling of the drive section chamber 224 by the passage of ultra-cold air into the drive section chamber 224. As may be realized, the narrow slots 263P (whether sealed or not sealed) may provide for increased thermal management, improved sample integrity and lower power usage by limiting or otherwise eliminating communication between the two chambers 223, 224.

The sample container holder 440 may be coupled to an outer drive shaft 440S of the coaxial drive shaft assembly so that the sample container holder 440 and the outer drive shaft rotate as a unit about axis RX. In one aspect the coaxial drive shaft assembly 460 may include an inner shaft having shaft portions 460S, 420S that may be formed as a single unit or coupled together in any suitable manner so as to rotate as a single unit where the inner shaft is disposed at least partly within the outer drive shaft 440S. The top pusher member 430 may be mounted to shaft portion 430S while the bottom pusher member 420 is mounted to shaft portion 420S so as to be located on opposite sides along the axis RX of the sample container holder 440. As may be realized, the outer drive shaft 440S may include an aperture through which the top pusher member 430 extends where the aperture may be configured to allow relative movement between the top pusher member 430 and the sample container holder 440. In one aspect each of the outer and inner drive shafts 440S, 430S, 420S may be coupled to a common rotary drive motor 401 so that the shafts 440S, 430S, 420S and hence the sample container holder 440, top pusher member 430 and bottom pusher member 420 rotate as a unit about the axis RX. The inner drive shaft formed by shaft portions 430S, 420S may be linearly moveable within the outer drive shaft 440S and be coupled to the at least one linear drive 201L2 for moving the top and bottom pusher members 430, 420 as a unit in the direction of arrow 299 relative to the sample container holder 440. In one aspect of the disclosed embodiment the coupling between each of the rotary drive motor(s) 401, 402, 403 and the at least one linear drive motor 201L2 with a respective shaft of the coaxial drive shaft assembly 460 may be a substantially direct coupling (e.g. no intervening belts or chains). For example, as shown in FIG. 4, each drive motor may include a drive gear DG1 (or any other suitable drive coupling) coupled to an output shaft of the drive motor that directly engages a driven gear DG2 (or any other suitable drive coupling) coupled substantially directly to a respective drive shaft without any intervening gears or other transmission members. In another aspect the rotor (e.g. moving portion of the motor) may be formed in or otherwise attached to a respective drive shaft such that the drive shaft effectively forms the rotor of the motor. In still other aspects of the disclosed embodiment any suitable transmission may be provided between the motor and respective drive shaft(s) for driving the transfer devices 201A, 201B as described herein.

As may be realized, the one or more rotary drive motor 401, 402, 403, the at least one linear drive motor 201L2 and the linear drive 201L1 may constitute a mixed Polar-Cartesian coordinate system that allows transfer of sample containers between sample holding locations 310 of a single sample rack 370, 570 or between different sample racks 370, 570 located in one or more sample trays 310TR with as few as three drive motors (e.g. as described above). In other aspects, more than three motors may be used, as described below, for the transfer of sample containers between sample holding locations 310 of a single sample rack 370, 570 or between different sample racks 370, 570 located in one or more sample trays 310TR. As may be realized, polar coordinate mapping of sample holding locations 310 may allow fast coordinated motion to the sample holding locations 310 on two sample trays 310TR by each transfer device 201A, 201B. In still other aspects the drive portion 202A may be mounted to the frame 210F so as to be fixed with respect to linear movement towards and away from the side walls 210LNA, 210LNB, 210LTA, 210LTB of the sample transfer module 200 (e.g. linear drive 201L1 is not provided) so that the transfer device 201A, 201B operates substantially in a pure Polar coordinate system.

In another aspect the shaft portion 430S may form a middle drive shaft and the shaft portion 420S may form an inner drive shaft where at least the inner drive shaft is independently rotatable relative to the outer drive shaft 440S. For example, the outer drive shaft 440S and the shaft portion 430S (e.g. middle drive shaft) may be coupled to a common rotary drive motor 401 so that the fop pusher member 430 and the sample container holder 440 rotate as a unit about axis RX while shaft portion 420S (e.g. inner drive shaft) is coupled to a separate rotary drive motor 402 so that the bottom pusher member 420 independently rotates about axis RX. In still another aspect the shaft portion 430S (e.g. middle drive shaft) may be coupled to a separate rotary drive motor 403 so that each of the top pusher member 430, sample container holder 440 and bottom pusher member 420 are independently rotatable relative to each other. In yet another aspect, where the shaft portion 430S and the shaft portion 420S respectively form middle and inner drive shafts, the shaft portion 430S may be coupled to one linear drive motor of the at least one drive motor 201L2 while the shaft portion 420S may be coupled to another linear drive motor of the at least one drive motor 201L2 so that each of the top pusher member 430 and the bottom pusher member 420 are independently movable in the direction of arrow 299 relative to the sample container holder 440.

As may be realized the rotary drive motor(s) 401, 402, 403 and the at least one linear drive motor 201L2 may include any suitable encoders or position detectors for determining, along with controller 170, a position of the transfer arm portion 400A along a length of the linear drive 201L1 for positioning the transfer arm portion 400A relative to the sample holding locations 310 within the sample tray 310TR. As may also be realized, the motor control adjustment of the stroke (e.g. amount of movement) of at least the top and bottom pusher members 430, 420 in the direction of arrow 299 may allow for the picking and placing of sample containers having different heights H (FIG. 4C).

Referring now to FIG. 4A the sample container holder 440 may include a gripper or sample container receiver 440A that is configured to hold one or more sample container types (e.g. different shapes of sample containers). In one aspect the gripper 440A may be an interchangeable gripper that is removable from the sample container holder 440 and replaceable with a different gripper 440A' having a different predetermined characteristic than the gripper 440A. The different predetermined characteristics may include, for example, an ability to hold a different size/shape sample container, movable gripper actuators, a configuration for punching sample containers to/from a sample tray, a configuration for pushing sample containers to/from a sample tray, a configuration to both punch and push sample containers to/from a sample tray, etc., where the term "punch" refers to transfer of a sample tube past a bottom surface of a sample tray and "push" refers to the transfer of a sample tube past a top surface of a sample tray (for ease of explanation the terms "punch" and "push" are generally referred to herein as "push"). In one aspect the gripper 440A may include a base member 440B that is coupled in any suitable manner to (so as to be interchangeable with other grippers) or integrally formed with the sample container holder 440. The base member 440B may include an aperture that passes through the base member 440B so as to form a sample container passage 440P through the base member 440B where the sample container passage 440P includes an axis AX extending through the passage and substantially along which sample containers SC are held by the gripper 440A. One or more biasing members 440S, such as springs or other resilient member, may be disposed at least partially within the sample container passage 440P for biasing a sample container SC (FIG. 4C) against a surface of the sample container passage 440P to effect a frictional engagement and retention of the sample container SC within the sample container passage 440P.

Figure 4B:
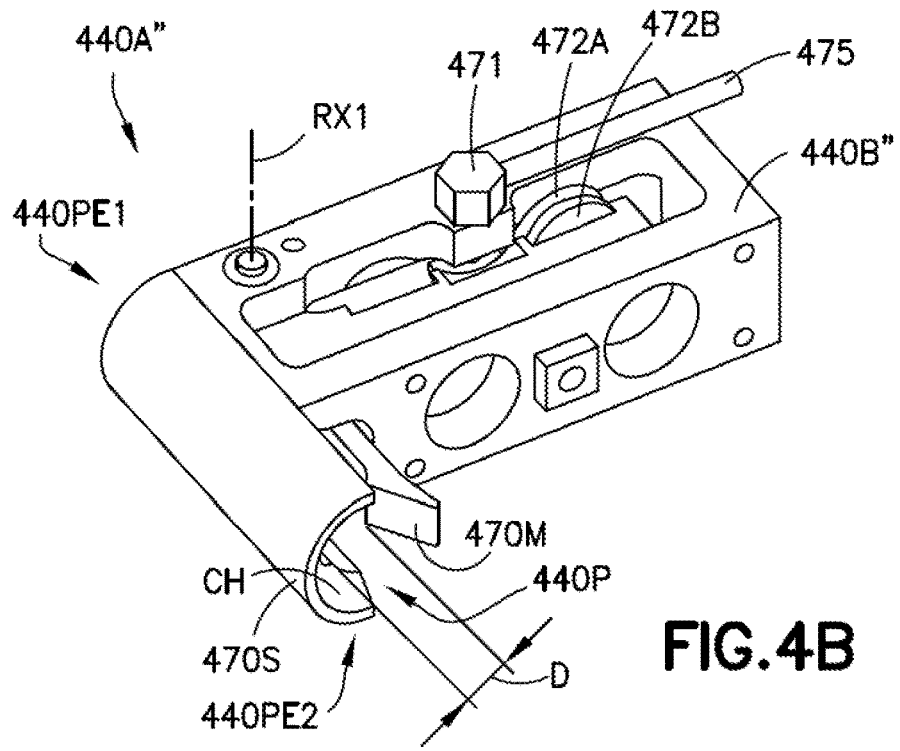
Figure 4C:
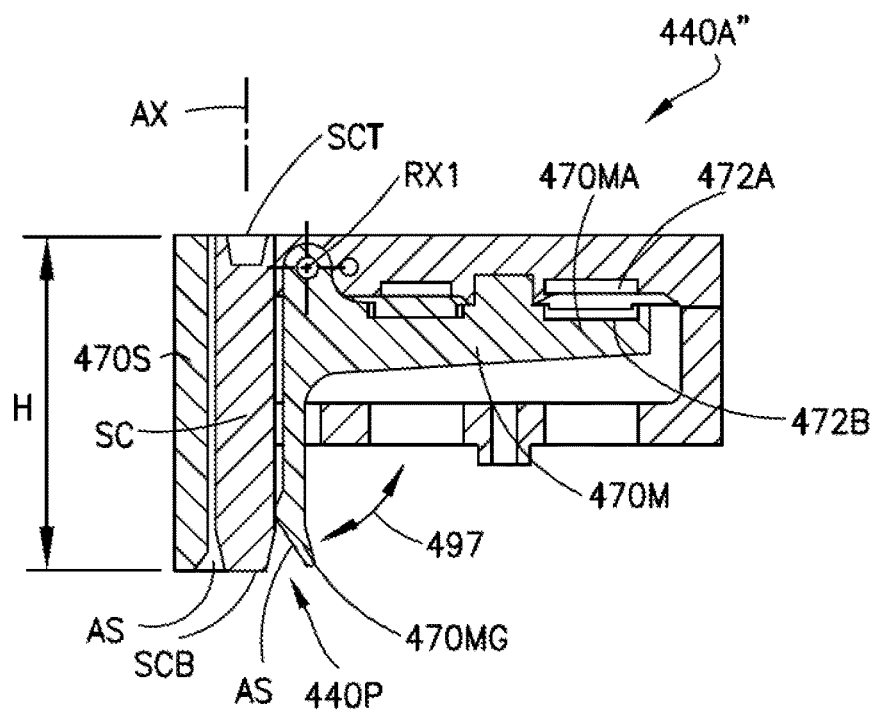

Referring now to FIGS. 4B and 4C, a gripper 440A" is illustrated in accordance with an aspect of the disclosed embodiment. The gripper 440A" may be substantially similar to gripper 440A however, the gripper 440A" may have at least one actuable or movable gripping member or finger 470M. For example, the base member 440B" may include a stationary finger 470S that forms at least part of the sample container passage 440P. In this aspect the stationary finger 470S has a semicircular shape so as to substantially conform with a shape of the sample container SC but in other aspects the stationary finger 470S may have any suitable shape. The movable finger 470M may be pivotally mounted to the base member 440B" in any suitable manner so as to be pivotable about an axis of rotation RX1. The movable finger 470M is illustrated as having a substantially "L" shaped configuration for exemplary purposes and in other aspects the movable finger 470M may have any suitable shape. The movable finger 470M may include a gripping portion 470MG and an actuator portion 470MA where the gripping portion 470MG is positioned relative to the base member 440B" to be in an opposing arrangement with the stationary finger 470S so that as the movable finger 470M pivots about axis RX1 the gripping portion 470MG moves towards the stationary finger 470S for gripping the sample container SC and away from the stationary finger 470S for releasing the sample container SC. In one aspect the movable finger 470M may be driven or otherwise actuated in any suitable manner such as with a solenoid type magnet arrangement. For example, a first magnetic member 472A may be positioned on the base member 440B" and a second magnetic member 472B may be positioned on the actuator portion 470MA of the movable finger 470M in an opposing relationship with the first magnetic member 472A. The magnetic members 472A, 472B may be any suitable magnetic members such as, for example, neodymium magnets. The first magnetic member 472A may be energized in any suitable way to either attract or repel the second magnetic member to respectively release or grip the sample container SC. In other aspects the magnetic members 472A, 472B may be positioned so that when the first magnetic member 472A is energized to either attract or repel the second magnetic member the sample container is respectively gripped or released. Any suitable sensor or detector 471 may be mounted to the base member 440B" and positioned relative to the movable finger 470M for detecting an open (e.g. the sample container is released) and/or closed (e.g. the sample container is gripped) position of the movable finger 470M. As may be realized, when the sample container SC is released by the gripper 440A" the sample container SC may freely fall from the gripper 440A" substantially without resistance from the gripper 440A". In other aspects any suitable resistance may be provided by the gripper 440A" so as to control a rate of descent of the sample container SC from the gripper 440A". Any suitable connector 475 may be connected to one or more of the sensor 471 and first magnetic member 472A and the controller 170 so that suitable control signals may be provided by the controller and sensor signal can be received by the controller for operating the gripper 440A".

In another aspect, still referring to FIGS. 4B and 4C the gripper 440A" may be a friction gripper where the magnetic members 472A, 472B are not selectively energized. For example, the magnetic members 472A, 472B may be arranged so as to repel each other biasing the movable finger 470M in a closed position for gripping the sample container SC. In other aspects the magnetic members 472A, 472B may be positioned relative to the base member 440B" and the movable finger 470M so that, an attractive force between the magnetic members 472A, 472B biases the movable finger 470M in the closed position. The gripping portion 470MG of the movable finger 470M in the biased position (without a sample container in the gripper) may be spaced from an opposing surface of the stationary finger 470S by a distance D where the distance D is smaller than a diameter, a width or a length (e.g. depending on the shape) of the sample container SC being gripped (e.g. the gripping portion 470MG is disposed at least partly within the sample container passage 440P) so that as the sample container SC is inserted into the gripper 440' the gripping portion 470MG is forced away from the stationary finger 470S by the sample container SC and the biasing force of the magnetic members 472A, 472B effect a compressive/friction force between the gripping portion 470MG, the stationary finger 470S and the sample container SC for gripping the sample container SC. In other aspects the biasing force may be provided in any suitable manner such as by springs or other suitable resilient or elastomeric member.

Figure 4D:
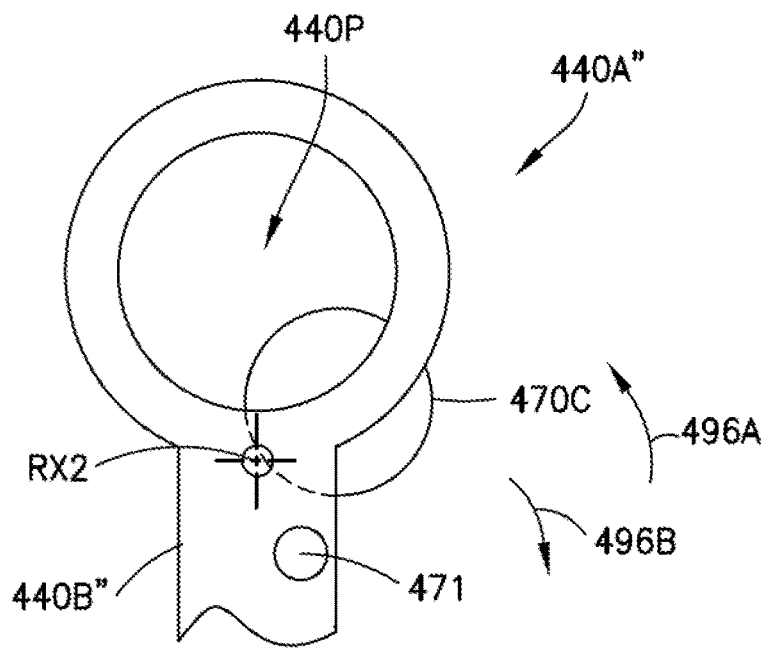

Referring now to FIG. 4D a gripper 440A''' is shown in accordance with another aspect of the disclosed embodiment. The gripper 440A''' may be substantially similar to gripper 440A however, in this aspect the gripper 440A''' includes a moving cam member 470C that engages a sample container in a manner substantially similar to that described above with respect to the movable finger 470M. For example, movement of the cam member 470C may be effected by attractive or repelling magnetic forces where the magnets are energized to cause movement of the cam member 470C in at least one of the directions 496A, 496B for opening and closing the gripper 440A''' in a manner substantially similar to that described above with respect to movable finger 470M. In other aspects, the cam member 470C may be biased in position within the sample container passage 440P such that as the sample container is moved into the sample container passage 440P the cam member is forced to move in the direction of arrow 496B by the sample container SC where a resilient or elastomeric member provides a resistive force on the cam member 470C for gripping sample container SC in a manner substantially similar to that described above. The cam member 470C may be coupled to the base member 440B''' in any suitable manner such as a pinned coupling so that the cam member pivots about axis RX2 in the direction of arrows 496A, 496B. As the cam member 470C is moved in the direction of arrow 496A at least partly into the sample container passage 440P the cam member 470C effects gripping of a sample container SC within the passage through engagement of the cam member with the sample container SC and engagement of the sample container with an interior wall of the sample container passage 440P. Any suitable sensors or detectors 471 may be mounted to the base member 440B''' for sensing when the gripper 440A''' is open or closed in a manner substantially similar to that described above.

In one aspect the components (e.g. base member 440B, 440B'', 440B''', stationary finger 470S, gripping portion 470MG of movable finger 470M) of the gripper 440A, 440A', 440A'', 440A''' forming the sample container passage 440P may include a chamfer or otherwise angled surface AS relative to an axis AX of the sample container passage 440P. The angled surface(s) AS may be provided at one or more ends 440PE1, 440PE2 so that at least one end 440PE1, 440PE2 of the sample container passage 440P has a lead in for insertion of the sample container SC into the sample container passage 440P. In one aspect where sample containers are inserted into the sample container passage from both ends 440PE1, 440PE2, the angled surface(s) AS may be disposed at both ends 440PE1, 440PE2 of the sample container passage 440P. In another aspect where the sample containers are inserted into the passage from only one end 440PE1, 440PE2 the end into which the sample container SC is inserted may include the angled surface(s) AS. The lead in formed by the angled surfaces AS may provide guidance (e.g. guiding surfaces) for directing the sample container into the gripper 440A, 440', 440A'', 440A''' and account for any misalignment between the sample container SC and the sample container passage 440P.

Figure 4E:
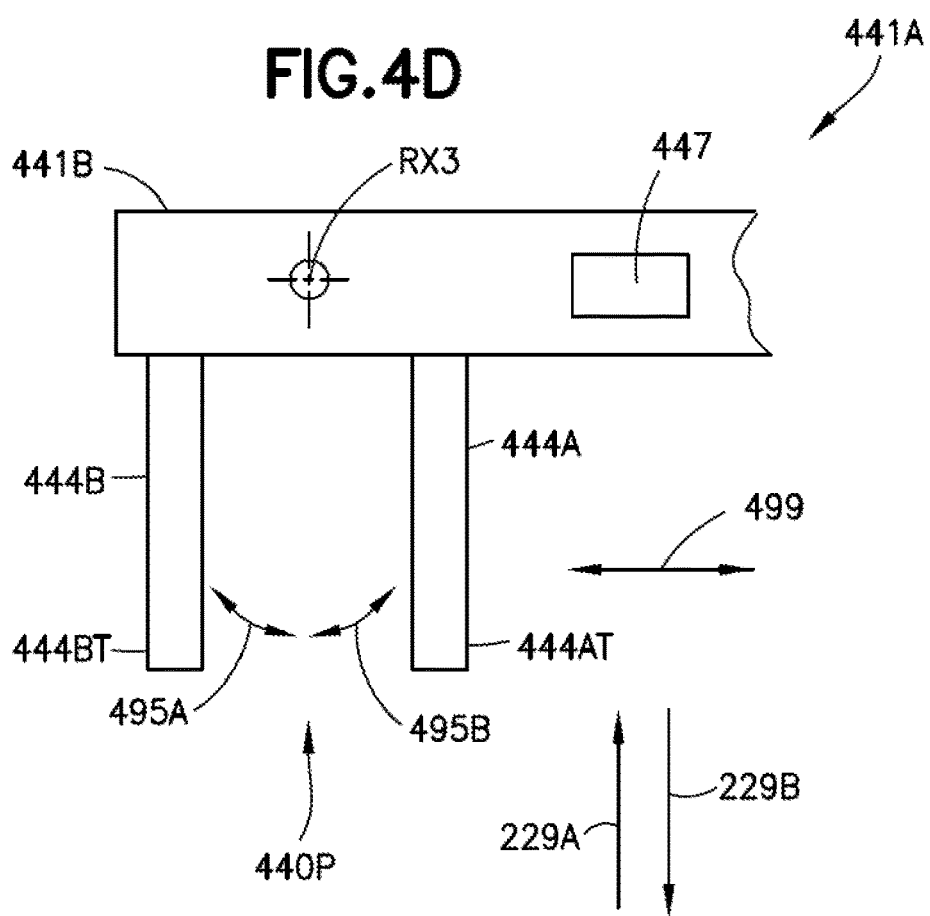

Referring now to FIG. 4E, in one aspect the gripper 441A may include a base member 441B and two movable fingers 444A, 444B coupled to the base member 441B. In this aspect the two movable fingers 444A, 444B may form a sample container passage 440P between the fingers, however, the sample container passage may not extend through the base member 441B (e.g. the sample container passage is not a through passage and only allows insertion of the sample container SC into the gripper 441A in one direction 299A). In other aspects the sample container passage may extend through the base member 441B to allow insertion of sample containers SC into the gripper in directions 299A, 299B. The gripper 441A may include any suitable actuator(s) (such as those described above) connected to the movable fingers 444A, 444B for gripping (e.g. closing the gripper) and releasing (e.g. opening the gripper) sample containers. In one aspect the movable fingers 444A, 444B may be mounted to the base member so as to move linearly relative to the base member 441B in the direction of arrow 499 towards and away from each other to respectively grip and release a sample container SC. In another aspect the movable fingers 444A, 444B may be mounted to the base member so as to pivot relative to a predetermined axis of rotation RX2 of the base member 441B for pivoting tips 444AT, 444BT (e.g. free ends) of the movable fingers 444A, 444B in the directions of arrows 495A, 495B, towards and away from each other to respectively grip and release a sample container SC. In other aspects, the gripper 441A may have only one movable finger (either one of fingers 444A, 444B) which may operate as described above relative to the other finger 444A, 444B (which is stationary) for gripping and releasing a sample container SC. In this aspect, the fop (e.g. upper) pusher member 430 may not be provided on the at least one transfer arm portion 400A (see FIG. 4A) such that the sample containers SC may be provided to the gripper 441A by, for example, the bottom (e.g. lower) pusher member 420 in a manner substantially similar to that described below and where the sample containers are placed into sample trays by gravity (e.g. the sample container falls freely from the gripper 441A when released for placement into a sample tray).

Referring again to FIG. 4A, the top pusher member 430 may include a sample container engagement portion 430A extending therefrom towards the gripper, such as gripper 440A for exemplary purposes only. Likewise the bottom pusher member 420 may also include a sample container engagement portion 420A extending therefrom towards the gripper. Each of the sample container engagement portions 430A, 420A may be substantially aligned with the axis AX and be configured to pass at least partially through the sample container passage 440P to effect transfer of sample containers to or from the gripper as described herein. In one aspect the sample container engagement portions 430A, 420A may have a push pin or rod configuration but in other aspects the sample container engagement portions 430A, 420A may have any suitable shape and size for at least a partial insertion into the sample container passage 440P and for engagement with the sample container SC.

Referring now to FIGS. 3A, 3B, 5A and 5B, as noted above, the sample selector module 200 may be configured to move sample containers SC between sample holding locations 310 within a single rack 370, 570, between multiple racks 370, 570 in a single tray 310TR and/or between multiple racks 370, 570 in multiple trays 310TR. The controller 170 may be configured to control automation of the sample selector module 200 (as described herein) with a required granularity for picking and placing sample containers SC to and from standard density trays 570 and high density trays 370 having any suitable spacing between sample container holding locations 310. The term "standard density tray" may refer to trays configured to hold an array of 24 sample containers, 48 sample containers or 96 sample containers. The term "high density tray" may refer to trays configured to hold an array of more than 96 sample containers. In one aspect the high density tray 370 may have a longitudinal (e.g. lengthwise) spacing X1 between sample holding locations 310 of about 8.25 mm and a lateral (e.g. widthwise) spacing X2 between sample holding locations 310 of about 9.00 mm. In another aspect the high density tray 370 may have a longitudinal spacing X1 between sample holding locations 310 of about 8.20 mm and a lateral spacing X2 between sample holding locations 310 of about 9.00 mm. In still other aspects the spacing X1, X2 between sample holding locations may be any suitable spacing.

As can be seen in FIGS. 5A and 5B the sample selector module 200 includes a single stack ST1 (e.g. one level) of sample tray holders 300A and a double stack ST2 (e.g. two stacked levels) of sample tray holders 300B, 300B1. Each stack ST1, ST2 includes a respective axis VX1, VX2 along which the respective sample tray holders 300A, 300B, 300B1 are arranged one over the other. The stacks ST1, ST2 may be spaced apart from one another so as to form an aisle ASL in which a respective transfer arm portion 400A travels. Each level in the stack may be arranged so that the level is disposed in a plane between the top pusher member 430 and the sample container holder 440 or in a plane between the sample container holder 440 and the bottom pusher member 420 so that sample containers may be pushed between the gripper of the sample container holder and a respective level of tray holders. In this aspect the sample tray holder 300A is holding a sample tray 310TR having one or more high density racks 370 thereon and the sample tray holders 300B, 300B1 are each holding a sample tray 310TR having one or more standard density racks 570A, 570B thereon. The rack 570A may be a source rack (e.g. a rack from which sample containers SC are removed or picked) and racks 370, 570B may be destination racks (e.g. racks to which sample containers are placed).

Referring also to FIGS. 3A, 4A and 9, in this aspect the top pusher member 430 and bottom pusher member 420 are arranged to move in the direction of arrows 299A, 299B as a unit relative to the sample container holder 440 (as described above). Also in this aspect the top pusher member 430, bottom pusher member 420 and the sample container holder 440 are arranged to rotate as a unit about axis RX (as described above). It is also noted that while gripper 440A is illustrated in other aspects the gripper may be any one of the grippers 440A, 440A', 440", 440A''', 441A described herein (noting that the gripper 441A may only receive sample containers delivered to the gripper in the direction of arrow 299A in the aspect where the passage 440P in the gripper 441A is not a through passage). In one aspect sample containers SC may be transferred between trays 570A, 570B stacked one above the other. The axis AX of the gripper may be positioned over a predetermined sample container holder location 310 of the source tray in any suitable manner (FIG. 9, Block 900). For example, the transfer arm portion 400A may be linearly moved in the direction of arrow 298 and/or rotated about axis RX for substantially aligning the axis AX with the predetermined sample container holder location 310 of the source tray 570A which in this example is disposed on a level between the top pusher member 430 and the sample container holder 440. In one aspect, the top and bottom pusher members 430, 420 may be actuated to move in the direction of arrow 299B to push a sample container from the predetermined sample holder location into the gripper 440A (FIG. 9, Block 905). It is noted that where the source tray is on a level disposed between the bottom pusher member 420 and the sample container holder 440 the top and bottom pusher members 430, 420 may be actuated to move in the direction of arrow 299A to push a sample container into the gripper 440A from the predetermined sample holder location of the source tray. The sample container SC may be transported by the transfer arm portion 400A to substantially align the axis AX of the gripper 440A with a predetermined sample container holding location 310 of a destination tray 570B, 370 (FIG. 9, Block 910. In one aspect the alignment of the gripper 440A with the predetermined sample container holding location 310 of a destination tray 570B, 370 may include moving the transfer arm portion linearly in the direction of arrow 298 and/or rotating the top pusher member 430, bottom pusher member 420 and the sample container holder 440 as a unit about axis RX (FIG. 9, Block 915). The top and bottom pusher members 430, 420 may be actuated to move in the direction of arrow 299B to push a sample container from the gripper 440A into the predetermined sample holder location of the destination tray 370, 570B (FIG. 9, Block 920). As may be realized, where the destination tray (which may be on the same level as the source tray or where the source tray is also the destination tray) is disposed on a level between the top pusher member 430 and the sample container holder 440 the top and bottom pusher members 430, 420 may be actuated to move in the direction of arrow 299A to push a sample container from the gripper 440A into the predetermined sample holder location of the destination tray.

In another aspect, when transferring a sample container SC between source and destination trays that are disposed one above the other, and where the source and destination sample container holding locations are substantially aligned with one another, the top and bottom pusher members 430, 420 may be actuated so that one of the sample container engagement portions 430A, 430B pushes the sample container from the predetermined sample container holding location 310 of the source tray through the sample container passage 440P (FIG. 9, Block 925) and into the predetermined sample container holding location 310 of the destination tray (FIG. 9, Block 920). In this aspect the sample container passage 440P of the gripper guides the transfer of the sample container SC between the source and destination sample container holding locations 310. As may be realized, the pass through transfer of sample containers (e.g. the transfer of the sample container completely through the gripper without moving the transfer arm portion 400A in the direction of arrow 298 or about the axis RX) may be performed regardless of whether one or more of the top pusher member 430, the bottom pusher member 420 and the sample container holder 440 are independently rotatable.

Figure 6A:
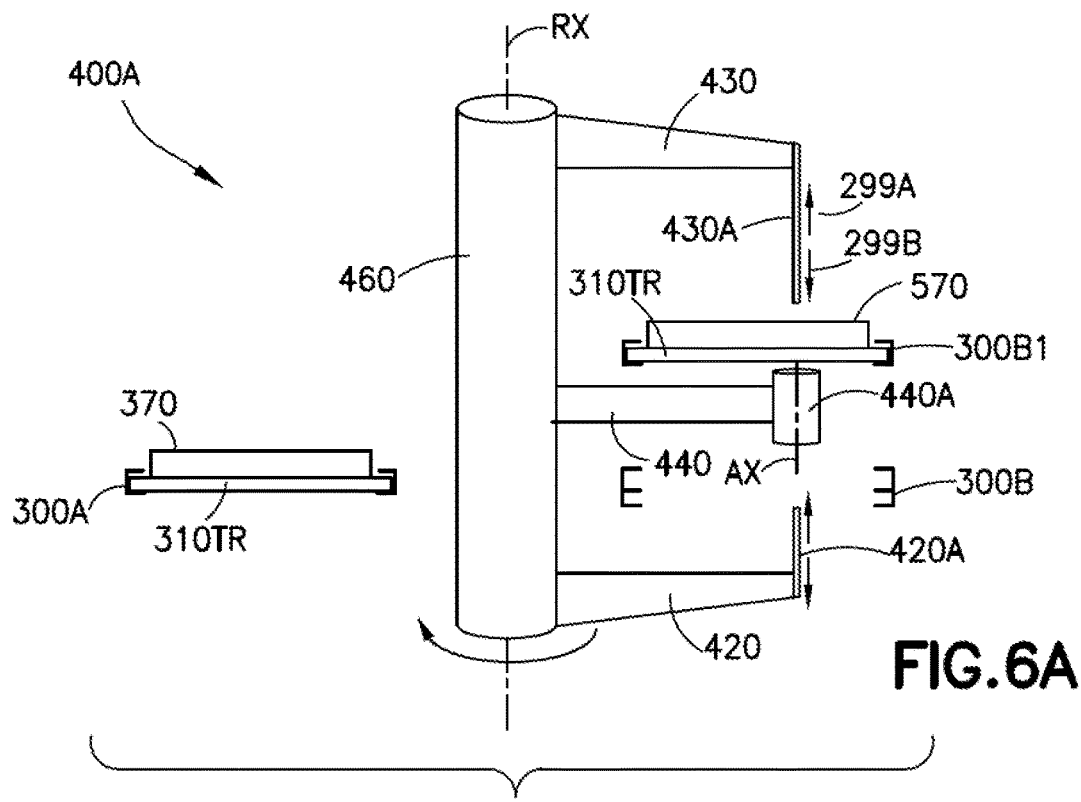
FIGS. 6A and 6B are schematic illustrations of a portion of the sample selector of FIGS. 2A through 2D in accordance with aspects of the disclosed embodiment.
Figure 6B:
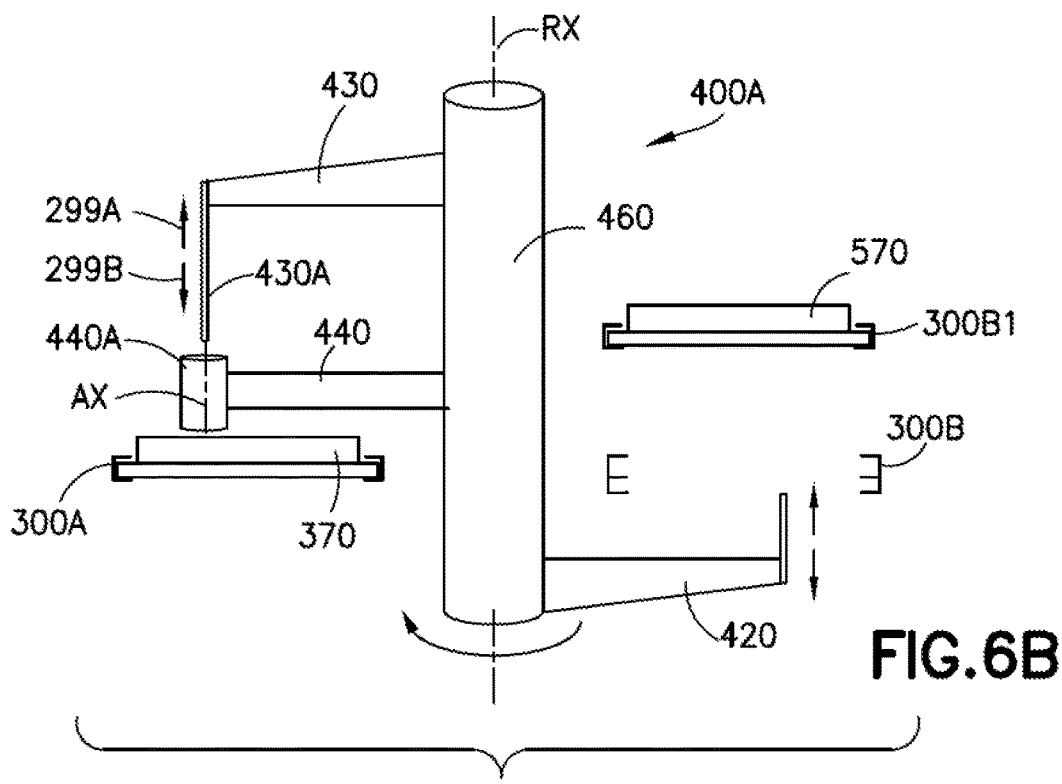

Still Referring to FIGS. 3A, 4A and 9 and also to FIGS. 6A and 6B, a transfer of a sample container between a source tray 570 disposed on a level between the top pusher member 430 and the sample container holder 440 and a destination tray 370 disposed on a level between the sample container holder 440 and the bottom pusher member 420 will be described. In this aspect at least the bottom pusher member 420 may be independently rotatable about axis RX relative to the sample container gripper 440. In this aspect the axis AX of the gripper may be positioned over a predetermined sample container holder location 310 of the source tray in any suitable manner (FIG. 9, Block 900). For example, the transfer arm portion 400A may be linearly moved in the direction of arrow 298 and/or the bottom pusher member 420, the top pusher member 430 and the sample container holder 440 (e.g. rotation of the bottom pusher member 420 is controlled independently from rotation of the upper pusher member 430 and sample container holder 440) are rotated about axis RX for substantially aligning the axis AX with the predetermined sample container holder location 310 of the source tray 570 which in this example is disposed on a level between the fop pusher member 430 and the sample container holder 440. In one aspect, at least the top pusher member 430 may be actuated to move in the direction of arrow 299B to push a sample container from the predetermined sample holder location into the gripper 440A (FIG. 9, Block 905). In one aspect the top and bottom pusher members 430, 420 may move in the direction of arrows 299A, 229B as a unit while in other aspects the top and bottom pusher members 430, 420 may be independently movable in the directions of arrows 299A, 299B. It is noted that where the source tray is on a level disposed between the bottom pusher member 420 and the sample container holder 440 at least the bottom pusher member 420 may be actuated to move in the direction of arrow 299A to push a sample container into the gripper 440A from the predetermined sample holder location of the source tray. The sample container SC may be transported by the transfer arm portion 400A to substantially align the axis AX of the gripper 440A with a predetermined sample container holding location 310 of a destination tray 570B, 370 (FIG. 9, Block 910). ID one aspect the alignment of the gripper 440A with the predetermined sample container holding location 310 of a destination tray 370 may include moving the transfer arm portion 400A linearly in the direction of arrow 298 and/or rotating the sample container holder 440 and the top pusher member 430 as a unit about axis RX (FIG. 9, Block 915). In one aspect the bottom pusher member 420 may also be rotated, albeit independently from the unitary rotation of the top pusher member 430 and the sample container holder 440. Here the top pusher member 430 may be actuated to move in the direction of arrow 299B to push a sample container from the gripper 440A into the predetermined sample holder location of the destination tray 370 (FIG. 9, Block 920). As may be realized, where the destination tray (which may be on the same level as the source tray or where the source tray is also the destination tray) is disposed on a level between the top pusher member 430 and the sample container holder 440 the bottom pusher member 420 may be actuated to move in the direction of arrow 299A to push a sample container from the gripper 440A into the predetermined sample holder location of the destination tray.

Referring to FIGS. 3A, 4A and 9 and also to FIGS. 7A and 7B, a transfer of a sample container between a source tray 370 disposed on a level between the bottom pusher member 420 and the sample container holder 440 and a destination tray 570 disposed on a level between the sample container holder 440 and the bottom pusher member 420 will be described. In this aspect both the top pusher member 430 and the bottom pusher member 420 may be independently rotatable about axis RX relative to the sample container gripper 440. In this aspect the axis AX of the gripper may be positioned over a predetermined sample container holder location 310 of the source tray in any suitable manner (FIG. 9, Block 900). For example, the transfer arm portion 400A may be linearly moved in the direction of arrow 298 and/or the sample container holder 440 may be rotated about axis RX for substantially aligning the axis AX with the predetermined sample container holder location 310 of the source tray 370. One or more of the top pusher member 430 and the bottom pusher member 420 (e.g. depending on a level of the source tray) may be independently rotated so that the respective sample container engagement portion 430A, 420A is substantially aligned with the axis AX and the predetermined sample holding location 310 of the source tray 370. In this example, the source tray 370 is disposed on a level between the bottom pusher member 420 and the sample container holder 440 so the bottom pusher member 420 is independently rotated about axis RX to remove the sample container SC from the source tray 370. In one aspect, at least the bottom pusher member 420 may be actuated to move in the direction of arrow 299A to push a sample container SC from the predetermined sample holder location into the gripper 440A (FIG. 9, Block 905). In one aspect the top and bottom pusher members 430, 420 may move in the direction of arrows 299A, 229B as a unit while in other aspects the top and bottom pusher members 430, 420 may be independently movable in the directions of arrows 299A, 299B. If is noted that where the source tray is on a level disposed between the top pusher member 430 and the sample container holder 440 at least the top pusher member 430 may rotated and actuated to move in the direction of arrow 299B to push a sample container into the gripper 440A from the predetermined sample holder location of the source tray. The sample container SC may be transported by the transfer arm portion 400A to substantially align the axis AX of the gripper 440A with a predetermined sample container holding location 310 of a destination tray 570B, 370 (FIG. 9, Block 910). In one aspect the alignment of the gripper 440A with the predetermined sample container holding location 310 of the destination tray 570 may include moving the transfer arm portion 400A linearly in the direction of arrow 298 and/or rotating the sample container holder 440 about axis RX (FIG. 9, Block 930). Here one or more of the top pusher member 430 and the bottom pusher member 420 may also be independently rotated so that the respective sample container engagement portion 430A, 420A is substantially aligned with the axis AX and the predetermined sample holding location 310 of the destination tray 570 (FIG. 9, Block 935). Here at least the top pusher member 430 may be actuated to move in the direction of arrow 299B to push a sample container from the gripper 440A into the predetermined sample holder location of the destination tray 570 (FIG. 9, Block 920). As may be realized, where the destination tray (which may be on the same level as the source tray or where the source fray is also the destination tray) is disposed on a level between the top pusher member 430 and the sample container holder 440 the bottom pusher member 420 may be actuated to move in the direction of arrow 299A to push a sample container from the gripper 440A into the predetermined sample holder location of the destination tray.

The exemplary sample container transfer described with respect to FIGS. 5A-7B involves sample container transport between high density trays 370 and standard density trays 570 and between multiple standard density trays. Referring now to FIGS. 8A and 8B sample container transfer may also be provided between multiple high density trays 370A, 370B in a manner substantially described above with respect to FIGS. 5A-7B. It is noted that the example illustrated in FIGS. 8A and 8B is similar to that illustrated in FIGS. 7A and 7B where the top and bottom pusher members 430, 420 are each independently rotatable relative to the sample container holder 440 such that sample container transfer is performed in a manner substantially similar to that described above with respect to FIGS. 7A and 7B.

It should be understood that while transfer of sample containers into the high density trays 370 as described herein are into trays 370 disposed on a level between the sample container holder 440 and the bottom pusher member, in other aspects transfer of sample containers into a high density tray 370 disposed on a level between the top pusher member 430 and the sample container holder 440 may occur in a manner substantially similar to that described above with respect to the standard density trays 570A. It should also be understood that where two source or two destination trays are disposed one above the other one or more of the bottom pusher member 420 and top pusher member 730 may be independently movable in the direction of arrows 299A, 299B relative to the other one of top pusher member 430 and bottom pusher member 420 as well as the sample container holder 440 to prevent unwanted insertion of a respective sample container engagement portion 430A, 420A into an occupied sample container holding location 310.

Referring now to FIGS. 10A and 10B in one aspect, the upper pusher arm 430 and the lower pusher arm 420 could be used to clamp a sample container SC between them for transfer of the sample container SC to and from the gripper 440A. For example, where the rack (such as rack 570 shown in FIGS. 10A and 10B or any other suitable rack such as rack 370) is disposed between the sample container holder 440 and the lower pusher arm 420 as illustrated in FIG. 10A, the upper pusher arm 430 may be moved in the direction of arrow 299B towards a top surface of the sample container SC such that the sample container engagement portion 430A extends through the gripper 440A to substantially contact the top surface of the sample container SC. The lower pusher arm 420 may be moved in the direction of arrow 299A towards the sample container so that the sample container engagement portion 420A substantially contacts a bottom surface of the sample container SC such that the sample container is clamped between the sample container engagement portions 430A, 420A.

Similarly, where the rack (such as rack 570 shown in FIGS. 10A and 10B or any other suitable rack such as rack 370) is disposed between the sample container holder 440 and the upper pusher arm 430 as illustrated in FIG. 10B, the lower pusher arm 420 may be moved in the direction of arrow 299A towards a bottom surface of the sample container SC such that the sample container engagement portion 420A extends through the gripper 440A to substantially contact the bottom surface of the sample container SC. The upper pusher arm 430 may be moved in the direction of arrow 299B towards the sample container so that the sample container engagement portion 430A substantially contacts the bottom surface of the sample container SC such that the sample container is clamped between the sample container engagement portions 430A, 420A.

As may be realized, after the container is clamped between the sample container engagement portions 430A, 420A, the sample container SC can be moved to the gripper 440A via simultaneous movement of the upper and lower pusher arms 420, 430 in one of the directions 299A, 299B depending on, for example, a location of the tray 570 relative to the gripper. Transfer of the sample container SC in this manner may provide higher alignment reliability by holding the sample container SC to its longitudinal axis. Also referring to FIG. 10C, the ends 1000A, 1000B of the sample container engagement portions 430A, 420A could be adapted to cradle the ends of the sample container and/or, referring to FIG. 10D, the sample container could have features 1001A, 1001B configured to register with the ends 1000A, 1000B of the sample container engagement portions 430A, 420A. In another aspect, the upper and lower pusher arms 430, 420 may clamp the sample container SC during rotation about axis RX such that one of the upper and lower pusher arms 430, 420 is moved in the direction of arrow 299A, 299B to clear the tray 570 and then move in the direction of arrow 299A, 299B to re-engage the sample container SC during rotation about axis RX.

In accordance with one or more aspects of the disclosed embodiment an apparatus includes a frame configured to hold sample holders in an array of sample holder locations, each sample holder being disposed in the array with a longitudinal axis of the sample holder extending outward of an array plane; a drive section connected to the frame; at least one transfer arm rotatably connected to the drive section so that each transfer arm rotates about a respective rotation axis oriented substantially parallel with the longitudinal axis of the sample holder, each transfer arm including a sample holder gripper configured to grip a sample holder; and at least one push member movably connected to the drive section, the at least one push member being distinct from the sample holder gripper and configured for linear movement along the longitudinal axis of the sample holder relative to a respective transfer arm and sample holder gripper, the at least one push member being configured so that engagement with at least a bottom or top surface of the sample holder effects longitudinal translation of the sample holder for one or more of capture and release of the sample holder by the respective transfer arm in the longitudinal direction.

In accordance with one or more aspects of the disclosed embodiment the sample holder gripper is configured to engage and grip the sample holder through a friction grip.

In accordance with one or more aspects of the disclosed embodiment the sample holder gripper includes a clamp member configured to actively engage and grip the sample holder through a clamp actuation.

In accordance with one or more aspects of the disclosed embodiment the at least one push member comprises another push member movably connected to the drive section, the other push member being distinct from the sample holder gripper and configured for linear movement along the longitudinal axis of the sample holder relative to the respective transfer arm and sample holder gripper, the other push member being configured so that engagement with at least a bottom or top surface of the sample holder effects longitudinal translation of the sample holder for one or more of capture and release of the sample holder by the respective transfer arm in the longitudinal direction.

In accordance with one or more aspects of the disclosed embodiment the at least one push member and the other push member are configured to clamp the sample holder between the at least one push member and the other push member.

In accordance with one or more aspects of the disclosed embodiment the respective transfer arm and the other push member are arranged so as to be located on opposite sides of a sample tray disposed within the apparatus where the sample tray being configured to hold at least one sample container.

In accordance with one or more aspects of the disclosed embodiment the respective transfer arm and the other push member are arranged so as to be located on a common side of a sample tray disposed within the apparatus where the sample tray being configured to hold at least one sample container.

In accordance with one or more aspects of the disclosed embodiment one or more of the at least one push member and the other push member are independently rotatable about the respective rotation axis relative to at least one of the respective transfer arm, sample holder gripper and each other.

In accordance with one or more aspects of the disclosed embodiment one or more of the at least one push member and the other push member rotate with the respective transfer arm as a unit about the respective rotation axis.

In accordance with one or more aspects of the disclosed embodiment the at least one push member is independently rotatable about the respective rotation axis relative to the respective transfer arm and sample holder gripper.

In accordance with one or more aspects of the disclosed embodiment the at least one push member rotates with the respective transfer arm as a unit about the respective rotation axis.

In accordance with one or more aspects of the disclosed embodiment the sample holder gripper of the respective transfer arm and the at least one push member are arranged so as to be located on opposite sides of a sample tray disposed within the apparatus where the sample tray being configured to hold at least one sample container.

In accordance with one or more aspects of the disclosed embodiment the sample holder gripper of the respective transfer arm and the at least one push member are arranged so as to be located on a common side of a sample fray disposed within the apparatus where the sample tray being configured to hold at least one sample container.

In accordance with one or more aspects of the disclosed embodiment the apparatus further includes an isolation member that divides the frame into isolated environments so that the drive section is isolated from an environment in which the at least one transfer arm and respective sample holder gripper operate.

In accordance with one or more aspects of the disclosed embodiment the isolation member includes at least one sealed penetration through which the at least one transfer arm extends.

In accordance with one or more aspects of the disclosed embodiment the at least, one transfer arm linearly moves in the array plane along a linear travel axis and the sealed penetration is configured to move with the at least one transfer arm along the linear travel axis.

In accordance with one or more aspects of the disclosed embodiment the sealed penetration comprises a slot through which the at least one transfer arm moves.

In accordance with one or more aspects of the disclosed embodiment the drive section includes a first drive for at least rotating at least one of the sample holder gripper and the at least one push member about the respective rotation axis, and a second drive for linearly translating the respective transfer arm and the at least one push member in a direction transverse to the respective rotation axis.

In accordance with one or more aspects of the disclosed embodiment the apparatus further includes at least one sample tray holder configured so that one or more sample trays are slid into a respective sample tray holding area, wherein the at least one transfer arm is configured to move sample holders between sample holding locations of the one or more sample trays.

In accordance with one or more aspects of the disclosed embodiment the at least one sample tray holder includes a retaining mechanism for holding the one or more sample trays in the respective sample tray holding area.

In accordance with one or more aspects of the disclosed embodiment the at least one transfer arm comprises two transfer arms disposed on opposite sides of a sample tray holding area within the frame.

In accordance with one or more aspects of the disclosed embodiment the frame defines a chamber arranged at least partly inside of a cold store.

In accordance with one or more aspects of the disclosed embodiment the frame is configured to mate with a closable opening in a wall of the cold store.

In accordance with one or more aspects of the disclosed embodiment the frame defines at least one closable opening within the cold store through which sample holders are inserted and removed from the frame, and includes a sliding closure magnetically sealed to the chamber for sealing a respective closable opening.

In accordance with one or more aspects of the disclosed embodiment the frame further defines a closable access opening, distinct from the at least one closable opening, configured to provide access to an interior of the frame.

In accordance with one or more aspects of the disclosed embodiment the closable access opening is disposed external to the cold store.

In accordance with one or more aspects of the disclosed embodiment the chamber is a portable chamber disposed on a transfer shuttle of the cold store.

In accordance with one or more aspects of the disclosed embodiment the sample holder gripper is an interchangeable gripper configured to be removed from and attached to the at least one transfer arm.

In accordance with one or more aspects of the disclosed embodiment an apparatus includes a frame; a sample tray holding area including at least a first and second tray holder disposed in a tray holder plane, each tray holder being configured for a sliding insertion of one or more sample trays into the tray holder and for holding the sample trays so that longitudinal axes of sample holders within the frays extend outward of the tray holder plane; a drive section connected to the frame; and at least one transfer arm connected to the drive section and being disposed in an aisle between the first and second tray holder, the at least one transfer arm including a rotation axis oriented substantially parallel with the longitudinal axes of the sample holders, a sample gripper, and a push member, the push member is configured for linear movement relative to the sample gripper, where the sample gripper and push member are arranged so as to rotate as a unit about the rotation axis.

In accordance with one or more aspects of the disclosed embodiment the push member is configured for longitudinal linear movement relative to the sample gripper and engagement with one or more of at least a top facing surface and at least a bottom facing surface of a sample holder effecting longitudinal translation of the sample holder between a sample tray and the sample gripper for one or more of capture and release of the sample holder by the sample gripper in the longitudinal direction.

In accordance with one or more aspects of the disclosed embodiment the push member comprises a first push member, the sample gripper and the first push member are arranged so as to be located on opposite sides of the sample tray disposed within the apparatus, the first push member being configured for at least partial insertion through a sample holding location of the sample tray, and engagement with a bottom facing surface or a top facing surface of the sample holder to transport the sample holder to the sample gripper.

In accordance with one or more aspects of the disclosed embodiment the push actuator comprises a second push member in opposing relation to the first push member, the sample gripper and the second push member are arranged so as to be located on a common side of the sample tray, the second push member being configured for at least partial insertion through the sample gripper, and engagement with the bottom facing surface or top facing surface of the sample holder to transfer the sample holder to the sample tray.

In accordance with one or more aspects of the disclosed embodiment the first push member and the second push member are configured to clamp the sample holder between the first push member and the second push member.

In accordance with one or more aspects of the disclosed embodiment the push actuator comprises a second push member, the sample gripper and the second push member are arranged so as to be located on opposite sides of another sample tray, the second push member being configured for at least partial insertion through the sample gripper, and engagement with another of the bottom facing surface or top facing surface of the sample holder to transfer the sample holder to the sample gripper.

In accordance with one or more aspects of the disclosed embodiment the sample gripper forms a sample holder passage configured to guide passage of the sample holder between the sample tray and the another sample tray and at least one of the first push member and second push member is configured to transfer the sample holder through the sample holder passage between the sample tray and the another sample tray.

In accordance with one or more aspects of the disclosed embodiment the apparatus further includes an isolation member that divides the frame into isolated environments so that the drive section is isolated from an environment in which the transfer arm operates.

In accordance with one or more aspects of the disclosed embodiment the isolation member includes a dynamically sealed penetration through which the at least one transfer arm member extends.

In accordance with one or more aspects of the disclosed embodiment the sealed penetration comprises a slot through which the at least one transfer arm moves.

In accordance with one or more aspects of the disclosed embodiment the frame defines a chamber arranged at least partly inside of a cold store.

In accordance with one or more aspects of the disclosed embodiment the frame is configured to mate with a closable opening in a wall of the cold store.

In accordance with one or more aspects of the disclosed embodiment the frame defines at least one closable opening within the cold store through which sample holders are inserted and removed from the frame, and includes a sliding closure magnetically sealed to the chamber for sealing a respective closable opening.

In accordance with one or more aspects of the disclosed embodiment the frame further defines a closable access opening, distinct from the at least one closable opening, configured to provide access to an interior of the frame.

In accordance with one or more aspects of the disclosed embodiment the closable access opening is disposed external to the cold store.

In accordance with one or more aspects of the disclosed embodiment the chamber is a portable chamber disposed on a transfer shuttle of the cold store.

In accordance with one or more aspects of the disclosed embodiment the at least one transfer arm includes a coaxial drive shaft assembly, the sample gripper being coupled to one drive shaft of the coaxial drive shaft assembly and the push member being coupled to another drive shaft of the coaxial drive shaft assembly.

In accordance with one or more aspects of the disclosed embodiment an apparatus includes a frame configured to hold an array of sample holders in sample trays; a drive section connected to the frame; a transfer arm at least rotatably connected to the drive section, the transfer arm having an axis of rotation and including a sample holder gripper, at least one pusher member mounted to the transfer arm so as to move linearly relative to the sample holder gripper and being configured to linearly transfer a sample holder between the sample trays and the sample holder gripper; and a controller connected to the drive section and being configured to effect, through movement of the transfer arm and the at least one pusher member, transfer of sample holders between sample trays having different sample holder holding capacities.

In accordance with one or more aspects of the disclosed embodiment the controller is configured to effect transfer of sample holders between sample trays having the same sample holder holding capacities.

In accordance with one or more aspects of the disclosed embodiment the array of sample holders is held in at least one sample holding plane and the sample holders have a longitudinal axis extending outwards of the sample holding plane, and the transfer arm has an axis of rotation substantially parallel with the longitudinal axis, where the sample holder gripper and the at least one pusher member rotate as a unit about the axis of rotation.

In accordance with one or more aspects of the disclosed embodiment the array of sample holders is held in at least one sample holding plane and the sample holders have a longitudinal axis extending outwards of the sample holding plane, and the transfer arm has an axis of rotation substantially parallel with the longitudinal axis, where the sample holder gripper and at least one of the at least one pusher member rotate independently about the axis of rotation.

In accordance with one or more aspects of the disclosed embodiment the at least one sample holding plane includes two stacked sample holding planes where the sample holder gripper is disposed between the two stacked sample holding planes, and the at least one pusher member is disposed on an opposite side of a respective one of the two stacked sample holding planes relative to the sample holder gripper.

In accordance with one or more aspects of the disclosed embodiment the sample holder gripper includes a sample holder passage configured to guide sample holder transfer from a sample tray disposed in a first one of the two stacked sample holding planes to sample tray in a second one of the two sample holding planes.

In accordance with one or more aspects of the disclosed embodiment the frame defines a housing having at least one chamber, the housing being configured for placement at least partially within a cold store.

In accordance with one or more aspects of the disclosed embodiment a method for transferring sample holders in a cold storage environment where the sample holders are held in an array of sample holder locations and being disposed in the array with a longitudinal axis of the sample holder extending outward of an array plane is provided. The method includes aligning a sample holder gripper and at least one push member with a predetermined sample holder in the array by at least rotating the sample holder gripper and the at least one push member about a common axis of rotation that is substantially parallel with the longitudinal axis, where the at least one push member is distinct from the sample holder gripper; and transferring the predetermined sample holder between the array and the sample holder gripper, for one or more of capture and release of the sample holder by the sample holder gripper in the longitudinal direction, by linearly moving the at least one push member relative to the sample holder gripper in the longitudinal direction for engaging at least a bottom or top surface of the sample holder and effecting longitudinal translation of the sample holder.

In accordance with one or more aspects of the disclosed embodiment aligning the sample holder gripper and the at least one push member with the predetermined sample holder includes rotating the sample holder gripper and the at least one push member as a unit about the common axis of rotation.

In accordance with one or more aspects of the disclosed embodiment aligning the sample holder gripper and the at least one push member with the predetermined sample holder includes independently rotating the sample holder gripper and one or more of the at least one push member about the common axis of rotation.

In accordance with one or more aspects of the disclosed embodiment aligning the sample holder gripper and the at least one push member with the predetermined sample holder includes linearly translating the sample holder gripper and the at least one push member as a unit in a direction transverse to the longitudinal axis.

In accordance with one or more aspects of the disclosed embodiment the array of sample holder locations are arranged in arrays in stacked levels where each level has a respective array plane, the method further includes transferring the predetermined sample holder from a sample holding location disposed in one stacked level to a sample holding location in another stacked level through a pass-through guide passage of the sample holder gripper.

In accordance with one or more aspects of the disclosed embodiment the at least one push member includes a first push member and a second push member, the method further includes clamping the predetermined sample holder between the first push member and the second push member for transferring the predetermined sample holder to the sample holder gripper.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the invention.

What is claimed is:

1. An apparatus comprising:
    a frame;
    a sample tray holding area including at least a first and a second tray holder disposed in a tray holder plane and separated from each other by an aisle between the first and the second tray holder, each tray holder being configured for a sliding insertion of one or more sample trays into the tray holder and for holding the sample trays so that longitudinal axes of sample holders within the trays extend outward of the tray holder plane;
    a drive section connected to the frame; and
    at least one transfer arm connected to the drive section and being disposed in the aisle between and separating the first and the second tray holder so as to extend through the aisle between the first and second tray holders, the at least one transfer arm including
        a rotation axis oriented substantially parallel with the longitudinal axes of the sample holders,
        a sample gripper, and
        a push member, the push member is configured for linear movement relative to the sample gripper,
        where the sample gripper and push member are arranged so that at least one of the sample gripper and push member rotates about the rotation axis.

2. The apparatus of claim 1, wherein the sample gripper and the push member are arranged so as to rotate about the rotational axis.

3. The apparatus of claim 1, wherein the sample gripper and the push member are arranged so as to rotate as a unit about the rotational axis.

4. An apparatus comprising:
    a frame;
    a sample tray holding area including at least a first and a second tray holder disposed in a tray holder plane and separated from each other by an aisle between the first and the second tray holder, each tray holder being configured for a sliding insertion of one or more sample trays into the tray holder and for holding the sample trays so that longitudinal axes of sample holders within the trays extend outward of the tray holder plane;
    a drive section connected to the frame;
    at least one transfer arm connected to the drive section and being disposed in the aisle between and separating the first and the second tray holder so as to extend through the aisle between the first and second tray holders, the at least one transfer arm including
        a rotation axis oriented substantially parallel with the longitudinal axes of the sample holders, and
        a sample gripper arranged so as to rotate about the rotational axis; and
    an isolation member that divides the frame into isolated environments so that the drive section is isolated from an environment in which the at least one transfer arm operates.

5. The apparatus of claim 4, wherein the at least one transfer arm includes a coaxial drive shaft assembly, the sample gripper being coupled to one drive shaft of the coaxial drive shaft assembly and the push member being coupled to another drive shaft of the coaxial drive shaft assembly.

6. The apparatus of claim 4, wherein the isolation member includes a dynamically sealed penetration through which the at least one transfer arm extends.

7. The apparatus of claim 6, wherein the dynamically sealed penetration comprises a slot through which the at least one transfer arm moves.

8. The apparatus of claim 4, wherein the at least one transfer arm further includes a push member, the push member being configured for linear movement relative to the sample gripper, and where the sample gripper and push member are arranged so that at least one of the sample gripper and the push member rotates about the rotational axis.

9. The apparatus of claim 8, wherein the sample gripper and the push member are arranged so as to rotate about the rotational axis.

10. The apparatus of claim 8, wherein the sample gripper and the push member are arranged so as to rotate as a unit about the rotational axis.

11. The apparatus of claim 8, wherein the push member is configured for longitudinal linear movement relative to the sample gripper and engagement with one or more of at least a top facing surface and at least a bottom facing surface of a sample holder effecting longitudinal translation of the sample holder between a sample tray and the sample gripper for one or more of capture and release of the sample holder by the sample gripper in a longitudinal direction.

12. The apparatus of claim 8, wherein the push member comprises a first push member, the sample gripper and the first push member are arranged so as to be located on opposite sides of the sample tray disposed within the apparatus, the first push member being configured for
    at least partial insertion through a sample holding location of the sample tray, and
    engagement with a bottom facing surface or a top facing surface of the sample holder to transport the sample holder to the sample gripper.

13. The apparatus of claim 12, wherein the push member comprises a second push member in opposing relation to the first push member, the sample gripper and the second push member are arranged so as to be located on a common side of the sample tray, the second push member being configured for
    at least partial insertion through the sample gripper, and
    engagement with the bottom facing surface or top facing surface of the sample holder to transfer the sample holder to the sample tray.

14. The apparatus of claim 12, wherein the push member comprises a second push member, the sample gripper and the second push member are arranged so as to be located on opposite sides of another sample tray, the second push member being configured for
    at least partial insertion through the sample gripper, and
    engagement with another of the bottom facing surface or top facing surface of the sample holder to transfer the sample holder to the sample gripper.

15. The apparatus of claim 14, wherein the sample gripper forms a sample holder passage configured to guide passage of the sample holder between the sample tray and the another sample tray and at least one of the first push member and the second push member is configured to transfer the sample holder through the sample holder passage between the sample tray and the another sample tray.

16. The apparatus of claim 4, wherein the frame defines a chamber arranged at least partly inside of a cold store.

17. The apparatus of claim 16, wherein the frame is configured to mate with a closable opening in a wall of the cold store.

18. The apparatus of claim 16, wherein the chamber is a portable chamber disposed on a transfer shuttle of the cold store.

19. The apparatus of claim 16, wherein the frame defines at least one closable opening within the cold store through which sample holders are inserted and removed from the frame, and includes a sliding closure magnetically sealed to the chamber for sealing a respective closable opening.

20. The apparatus of claim 19, wherein the frame further defines a closable access opening, distinct from the at least one closable opening, configured to provide access to an interior of the frame.

21. The apparatus of claim 20, wherein the closable access opening is disposed external to the cold store.

\* \* \* \* \*